US009783643B2

(12) United States Patent
Hori et al.

(10) Patent No.: US 9,783,643 B2
(45) Date of Patent: Oct. 10, 2017

(54) SILICONE MODIFIED BY LONG-CHAIN HYDROCARBON GROUP-CONTAINING DIGLYCERIN DERIVATIVE, AND USE THEREOF

(71) Applicant: DOW CORNING TORAY CO., LTD., Tokyo (JP)

(72) Inventors: Seiji Hori, Fukui (JP); Sayuri Sawayama, Chiba (JP); Seiki Tamura, Chiba (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/908,715

(22) PCT Filed: Jun. 10, 2014

(86) PCT No.: PCT/JP2014/065832
§ 371 (c)(1),
(2) Date: Jan. 29, 2016

(87) PCT Pub. No.: WO2014/200111
PCT Pub. Date: Dec. 18, 2014

(65) Prior Publication Data
US 2016/0177038 A1 Jun. 23, 2016

(30) Foreign Application Priority Data
Jun. 13, 2013 (JP) ................. 2013-124968

(51) Int. Cl.
| | | |
|---|---|---|
| *C08G 77/38* | (2006.01) | |
| *A61Q 19/00* | (2006.01) | |
| *A61K 8/893* | (2006.01) | |
| *A61K 8/89* | (2006.01) | |
| *B01F 17/54* | (2006.01) | |
| *C08L 83/04* | (2006.01) | |
| *A61Q 1/02* | (2006.01) | |
| *A61Q 3/02* | (2006.01) | |
| *A61Q 15/00* | (2006.01) | |
| *A61Q 17/04* | (2006.01) | |
| *A61Q 5/02* | (2006.01) | |
| *A61Q 5/06* | (2006.01) | |
| *A61Q 5/10* | (2006.01) | |
| *A61Q 5/12* | (2006.01) | |

(52) U.S. Cl.
CPC ............... *C08G 77/38* (2013.01); *A61K 8/89* (2013.01); *A61K 8/893* (2013.01); *A61Q 19/00* (2013.01); *B01F 17/0071* (2013.01); *C08L 83/04* (2013.01); *A61K 2800/10* (2013.01); *A61K 2800/48* (2013.01); *A61K 2800/596* (2013.01); *A61Q 1/02* (2013.01); *A61Q 3/02* (2013.01); *A61Q 5/02* (2013.01); *A61Q 5/06* (2013.01); *A61Q 5/10* (2013.01); *A61Q 5/12* (2013.01); *A61Q 15/00* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 5,144,054 A | 9/1992 | Shioya et al. | |
| 8,784,787 B2* | 7/2014 | Tamura | A61K 8/894 424/70.19 |
| 9,090,755 B2* | 7/2015 | Nakanishi | A61K 8/891 |
| 2004/0146472 A1 | 7/2004 | Nakanishi | |
| 2005/0084467 A1 | 4/2005 | Miyanaga | |
| 2005/0261133 A1 | 11/2005 | Nakanishi et al. | |
| 2008/0311060 A1* | 12/2008 | Sakuta | A61K 8/891 424/59 |
| 2010/0004201 A1 | 1/2010 | Matsuo et al. | |
| 2011/0251417 A1* | 10/2011 | Okawa | A61K 8/894 556/445 |
| 2012/0269747 A1* | 10/2012 | Iimura | A61Q 19/00 424/59 |
| 2012/0269748 A1 | 10/2012 | Tamura et al. | |
| 2012/0269875 A1 | 10/2012 | Tamura et al. | |
| 2013/0102686 A1* | 4/2013 | Tamura | A61K 8/892 514/772 |

(Continued)

FOREIGN PATENT DOCUMENTS

| | | | |
|---|---|---|---|
| EP | 2492301 A1 | 8/2012 | |
| EP | 2716687 A1 | 4/2014 | |

(Continued)

OTHER PUBLICATIONS

PCT/JP2014/065832 International Search Report dated Sep. 9, 2014, 3 pages.
English language abstract and machine translation for JPH07-238170 (A) extracted from https://www4.j-platpat.inpit.go.jp database on Feb. 1, 2016, 28 pages.
English language abstract and machine translation for JPH10-310504(A) extracted from http://worldwide.espacenet.com database on Feb. 1, 2016, 12 pages.
English language abstract and machine translation for JPH10-310505(A) extracted from http://worldwide.espacenet.com database on Feb. 2, 2016, 11 pages.
English language abstract and machine translation for JPH10-310506(A) extracted from http://worldwide.espacenet.com database on Feb. 2, 2016, 12 pages.
English language abstract and machine translation for JPH10-310507(A) extracted from http://worldwide.espacenet.com database on Feb. 2, 2016, 11 pages.

(Continued)

*Primary Examiner* — Robert S Loewe
(74) *Attorney, Agent, or Firm* — Warner Norcross & Judd LLP

(57) ABSTRACT

The present invention provides a glycerin-modified silicone which has an excellent emulsification/dispersion performance and thickening effect when used alone, particularly when the oil phase is a continuous phase.
The present invention is a specific diglycerin derivative-modified silicone having a long-chain hydrocarbon group at a prescribed ratio in a molecule and having as a hydrophilic group only a diglycerin derivative group not having an oxyalkylene structure with an average value of the number of repetitions of oxyalkylene units of two or more; and a composition containing the diglycerin derivative-modified silicone.

18 Claims, No Drawings

(56) References Cited

U.S. PATENT DOCUMENTS

| | | |
|---|---|---|
| 2014/0004065 A1 | 1/2014 | Souda et al. |
| 2014/0161758 A1* | 6/2014 | Tamura ............... A61K 8/895 424/78.02 |
| 2014/0193353 A1 | 7/2014 | Tamura et al. |
| 2014/0194532 A1 | 7/2014 | Tamura et al. |
| 2014/0364394 A1 | 12/2014 | Tamura et al. |
| 2015/0004107 A1 | 1/2015 | Sawayama et al. |
| 2015/0011656 A1 | 1/2015 | Tamura et al. |
| 2016/0008260 A1 | 1/2016 | Creutz et al. |

FOREIGN PATENT DOCUMENTS

| | | | |
|---|---|---|---|
| EP | 2716688 A1 | 4/2014 | |
| EP | 2939999 A1 | 11/2015 | |
| EP | 2940063 A1 | 11/2015 | |
| JP | H04-108795 A | 4/1992 | |
| JP | H07-238170 A | 9/1995 | |
| JP | H10-310504 A | 11/1998 | |
| JP | H10-310505 A | 11/1998 | |
| JP | H10-310506 A | 11/1998 | |
| JP | H10-310507 A | 11/1998 | |
| JP | H10-310508 A | 11/1998 | |
| JP | H10-310509 A | 11/1998 | |
| JP | 2002-179798 A | 6/2002 | |
| JP | 2004-339244 A | 12/2004 | |
| JP | 3625471 B2 | 3/2005 | |
| JP | 3678420 B2 | 8/2005 | |
| JP | 2005-344076 A | 12/2005 | |
| JP | 2006-218472 A | 8/2006 | |
| JP | 2012-046507 A | 3/2012 | |
| JP | 2012149052 A | 8/2012 | |
| JP | WO 2012165228 A1 * | 12/2012 | ............ C08G 77/46 |
| JP | 2013-151656 A | 8/2013 | |
| JP | 2013-151659 A | 8/2013 | |
| JP | 2013-151660 A | 8/2013 | |
| JP | 2014-129476 A | 7/2014 | |
| WO | WO03075864 A1 | 9/2003 | |
| WO | WO2007109240 A2 | 9/2007 | |
| WO | WO2009006091 A2 | 1/2009 | |
| WO | WO2011028765 A1 | 3/2011 | |
| WO | WO2011028770 A1 | 3/2011 | |
| WO | WO2011049247 A1 | 4/2011 | |
| WO | WO2011049248 A1 | 4/2011 | |
| WO | WO2012015070 A1 | 2/2012 | |
| WO | WO2012165237 A1 | 6/2012 | |
| WO | WO2012165235 A1 | 12/2012 | |
| WO | WO2013100169 A1 | 7/2013 | |
| WO | WO2013103147 A1 | 7/2013 | |
| WO | WO2014104255 A1 | 7/2014 | |
| WO | WO2014104256 A1 | 7/2014 | |
| WO | WO2014104258 A1 | 7/2014 | |

OTHER PUBLICATIONS

English language abstract and machine translation for JPH10-310508 (A) extracted from http://worldwide.espacenet.com database on Feb. 2, 2016, 14 pages.

English language abstract and machine translation for JPH10-310509 (A) extracted from http://worldwide.espacenet.com database on Feb. 2, 2016, 12 pages.

English language abstract for WO03075864 (A1) extracted from http://worldwide.espacenet.com database on Feb. 1, 2016, 1 page.

English language abstract and machine translation for JP3678420 (B2) extracted from hhttps://www4.j-platpat.inpit.go.jp database on Feb. 3, 2016, 30 pages.

English language abstract and machine translation for JP2014-129476 (A) extracted from https://www4j-platpatinpit.go.jp database on Feb. 1, 2016, 91 pages.

English language abstract and machine translation for JP3625471 (B2) extracted from https://www4.j-platpat.inpit.go.jp database on Feb. 3, 2016, 18 pages.

\* cited by examiner

SILICONE MODIFIED BY LONG-CHAIN HYDROCARBON GROUP-CONTAINING DIGLYCERIN DERIVATIVE, AND USE THEREOF

CROSS-REFERENCE TO RELATED APPLICATIONS

This application is the National Stage of International Application No. PCT/JP2014/065832 filed on 10 Jun. 2014, which claims priority to and all advantages of Japanese Patent Application No. 2013-124968 filed on 13 Jun. 2013, the content of which is hereby incorporated by reference.

TECHNICAL FIELD

The present invention relates to a diglycerin derivative-modified silicone having a long-chain hydrocarbon group at a prescribed ratio in a molecule and having as a hydrophilic group only a diglycerin derivative group not having an oxyalkylene structure with an average value of the number of repetitions of oxyalkylene units of two or more; and the use thereof.

BACKGROUND ART

In recent years, there has been a global trend of improving the composition of end consumer products such as cosmetic products to products which do not contain polyoxyethylene as a whole. For example, in Germany, there is an increasing demand to replace raw materials containing polyether groups with non-polyether raw materials that do not contain polyether groups in response to negative perceptions stemming from examinations by consumer-oriented information-providing magazine companies regarding the safety of products containing polyoxyethylene (PEG). In addition, in South Korea, there is an increasing interest in non-polyether-based silicone surfactants due to concerns that since formalin can be produced by the oxidative degradation of polyoxyethylene (PEG), products containing polyoxyethylene may cause skin irritation.

In concert with the global trends described above, there is a demand to evolve technology in the field of silicone-based surfactants from conventional polyether-modified silicone to non-polyether-based silicone. Further, glycerin-modified silicone has attracted attention as a surfactant having enhanced safety since the oxidative stability of glycerin-modified silicone is considered to be superior to that of polyether-modified silicone.

However, conventional glycerin-modified silicone has a substantial problem. This problem is that even if there was a desire to use a conventional glycerin-modified silicone as an emulsifier for a water-in-oil emulsion, it could not withstand use in the actual formulation of a cosmetic composition since its emulsification capacity, its ability to accommodate various oil agents, and the like are low. Therefore, it has been unavoidable to use polyether-modified silicone, which is a more reliable emulsifier, in combination with glycerin-modified silicone, and it has not been possible to achieve the goal of improving cosmetic compositions to formulations not containing polyoxyethylene (also called "PEG-FREE" hereafter). Moreover, there has not been any reports regarding materials suitable as thickening emulsifiers for a water-in-oil emulsion in technologies related to conventional glycerin-modified silicone (Patent Documents 1 to 6).

On the other hand, research focusing on diglycerin-modified silicone is scarce, such as that appearing in Patent Document 7. However, the glyceryl ether-modified organo(poly)siloxane having a specific structure reported therein has poor compatibility with various organic oils, and a stable water-in-oil emulsion cannot be obtained with a formulation having a high ratio of organic oil in the oil phase. This leads to the problem that separation is induced over time or due to temperature. Therefore, it has not been possible to use the substance alone as an emulsifier in such formulations, and it has been necessary to use the substance in combination with long-chain alkyl/polyether-co-modified silicone or the like.

In Patent Document 8, the present applicant therefore proposes using a co-modified organopolysiloxane copolymer having a group having a carbosiloxy dendron structure and a hydrophilic group such as glycerin or polyhydric alcohol in a molecule as a surfactant, powder treatment agent, or a surface treatment agent that can be suitably used in the cosmetic field, in particular. In particular, in Practical Example 13 of Patent Document 8, the present applicant proposes a novel glycerin derivative-modified silicone No. 13 having a group having a siloxane dendron structure, a tetraglycerin derivative group, and a diglycerin derivative group in each molecule, and proposes a water-in-oil emulsion composition (Formulation Example 5) and an external skin preparation in the form of a water-in-oil emulsion (Formulation Example 33) thereof. Although the glycerin derivative-modified silicone proposed here makes it possible to prepare a particularly stable water-in-oil emulsion when an oil phase is the silicone oil main component, an emulsion of low viscosity tends to be obtained. In addition, emulsion itself is difficult for a system in which a non-polar organic oil with a relatively large molecular weight such as a mineral oil serves as the main component of the oil phase. There still remains room for improvement regarding the emulsion stability thereof—in particular, the long-term storage stability at high temperature.

Moreover, in Patent Document 9, the present applicant has reported that among the co-modified organopolysiloxanes described in Patent Document 8, specific co-modified organopolysiloxanes in which the average degree of polymerization of the glycerin portion is in a range of 3 to 5 are particularly useful as thickening agents or gelling agents for oil-based raw materials. However, when using these materials in an emulsion system, the stability of the emulsion can be ensured only by thickening or structuring the oil phase, and the emulsion particle size itself is as large as in the case of conventional glycerin-modified silicones. Therefore, there still remains room for improvement from the perspective of the emulsion capacity or the perspective of the reliability as an emulsifier.

CITATION LIST

Patent Literature

Patent Document 1: Japanese Patent No. 26131248 (Japanese Unexamined Patent Application Publication No. H04-108795A)
Patent Document 2: Japanese Patent No. 3976226B (Japanese Unexamined Patent Application Publication No. 2002-179798A)
Patent Document 3: Japanese Patent No. 4485134B (Japanese Unexamined Patent Application Publication No. 2004-339244A)
Patent Document 4: Japanese Unexamined Patent Application Publication No. 2005-344076A Patent Document 5: Japanese Unexamined Patent Application Publication No. 2006-218472A
Patent Document 6: Japanese Patent No. 3678420 (WO/2003/041664)
Patent Document 7: Japanese Patent No. 3389311 (Japanese Unexamined Patent Application Publication No. H07-23817A)
Patent Document 8: WO/2011/049248
Patent Document 9: WO/2011/049247
Patent Document 10: Japanese Unexamined Patent Application Publication No. 2012-046507A

SUMMARY OF INVENTION

Technical Problem

The present invention was conceived in order to solve the problems described above, and a first object thereof is to provide a glycerin-modified silicone which itself has an excellent emulsification/dispersion performance and thickening effect, particularly when the oil phase is a continuous phase. Specifically, a first object of the present invention is to provide a diglycerin derivative-modified silicone which minutely and stably emulsifies and disperses an aqueous (or polyol) phase, is capable of forming an emulsion having high viscosity, and is capable of providing a composition having excellent stability over time or at high temperature, not only when the oil phase comprises a silicone oil or a mixed oil of a silicone oil and a non-silicone oil (ester-based oil or the like), but also when the oil phase primarily consists of a non-polar organic oil such as a mineral oil or isohexadecane, which has been difficult with conventional glycerin-modified silicones.

In addition, a second object of the present invention is to provide a composition which is essentially capable of overcoming problems associated with the oxidative degradation of polyoxyethylene (PEG), is stable regardless of the type of the oil phase, and is capable of forming an emulsion having high viscosity.

Solution to Problem

As a result of conducting dedicated research, the present inventors discovered that the first object described above can be achieved by a diglycerin derivative-modified silicone comprising: a halogen atom-substituted or unsubstituted monovalent hydrocarbon group having from 9 to 30 carbon atoms at a ratio of at least 0.5 mass % in a molecule; and as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, and the diglycerin derivative-modified silicone not having other hydrophilic groups in the molecule. The present inventors thereby completed the present invention.

In addition, the present inventors discovered that the second object described above can be achieved by a composition containing the diglycerin derivative-modified silicone described above, and thereby completed the present invention.

A first aspect of the present invention is a diglycerin derivative-modified silicone comprising a halogen atom-substituted or unsubstituted monovalent hydrocarbon group having from 9 to 30 carbon atoms in a molecule and having as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %.

The other hydrophilic group is preferably a (poly)glycerin derivative group excluding a glycerin derivative group having an average value of the number of repetitions of glycerin units in a range of 1.5 to 2.4, or an oxyalkylene derivative group having an oxyalkylene structure with an average value of the number of repetitions of oxyalkylene units of two or more.

The number average molecular weight of the diglycerin derivative-modified silicone of the present invention is preferably at least 20,000.

The diglycerin derivative-modified silicone of the present invention can be represented by the following general formula (1):

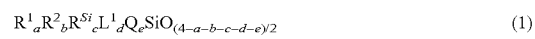

$$R^1_a R^2_b R^{Si}_c L^1_d Q_e SiO_{(4-a-b-c-d-e)/2} \qquad (1)$$

(In general formula (1), $R^1$ is a halogen atom-substituted or unsubstituted monovalent hydrocarbon group having from 1 to 8 carbon atoms, an alkoxy group, a hydrogen atom, or a hydroxyl group.

$R^2$ is a halogen atom-substituted or unsubstituted monovalent hydrocarbon group having from 9 to 30 carbon atoms.

$R^{Si}$ is a chain oraanosiloxane arouo represented by the following general formula (2-1):

[Formula 1]

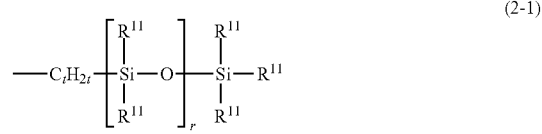

(wherein $R^{11}$ is a halogen atom-substituted or unsubstituted monovalent hydrocarbon group having from 1 to 30 carbon atoms, a hydroxyl group, or a hydrogen atom, and at least one of the $R^{11}$ moieties is the monovalent hydrocarbon group; t is a number in a range of 2 to 10; and r is a number in a range of 1 to 500); or the following general formula (2-2):

[Formula 2]

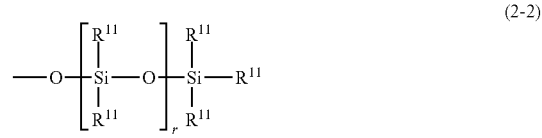

(wherein $R^{11}$ and r are synonymous with those described above).

$L^1$ is a silylalkyl group having a siloxane dendron structure represented by the following general formula (3) when i=1:

[Formula 3]

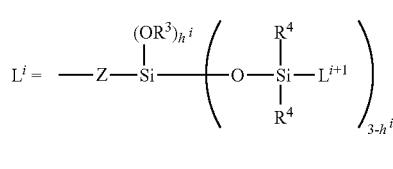
(3)

(wherein $R^3$ is a halogen atom-substituted or unsubstituted, straight-chain or branched monovalent hydrocarbon group having from 1 to 30 carbon atoms; $R^4$ is each independently an alkyl group or phenyl group having from 1 to 6 carbon atoms; Z is a divalent organic group; i is the generation of the silylalkyl group represented by $L^i$ and is an integer of 1 to k when k is a number of generations serving as a number of repetitions of the silylalkyl group; the number of generations k is an integer of 1 to 10; $L^{i+1}$ is the silylalkyl group when i is less than k, and $R^4$ when i=k; and $h^i$ is a number in a range of 0 to 3);

Q is a glycerin derivative group having an average value of the number of repetitions of glycerin units in a range of 1.5 to 2.4; and a, b, c, d, and e are numbers in ranges so that $0 \leq a \leq 2.5$, $0 < b \leq 1.5$, $0 \leq c+d \leq 1.5$, and $0.001 \leq e \leq 1.5$}

The glycerin derivative group described above is preferably a diglycerin derivative group-containing organic group bonded to a silicon atom via a divalent linking group and comprising at least one type of glycerin unit selected from hydrophilic units represented by the following structural formulae (4-1) to (4-3), the number of repetitions thereof being in a range of 1.5 to 2.4 on average (however, the substance does not have an oxyalkylene structure having an average value of the number of repetitions of oxyalkylene units of two or more in the same group).

[Formula 4]

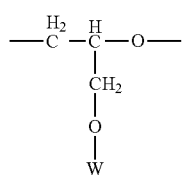
(4-1)

(wherein W is a hydrogen atom or an alkyl group having from 1 to 20 carbon atoms.)

[Formula 5]

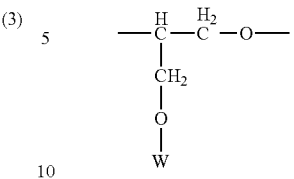
(4-2)

(wherein W is synonymous with the group described above.)

[Formula 6]

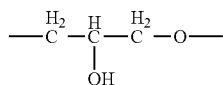
(4-3)

The glycerin derivative group is preferably a diglycerin derivative group-containing organic group represented by the following general formula (5-1).

[Formula 7]

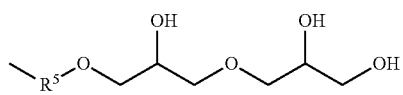
(5-1)

(wherein $R^5$ is a divalent organic group that does not have an oxyalkylene structure having an average value of the number of repetitions of oxyalkylene units of two or more) or the following general formula (5-2):

[Formula 8]

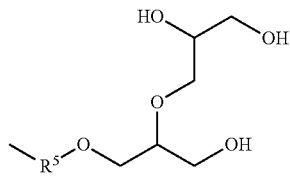
(5-2)

(wherein $R^5$ is as described above.)

The glycerin derivative-modified silicone of the present invention is preferably represented by the following structural formula (1-1):

[Formula 9]

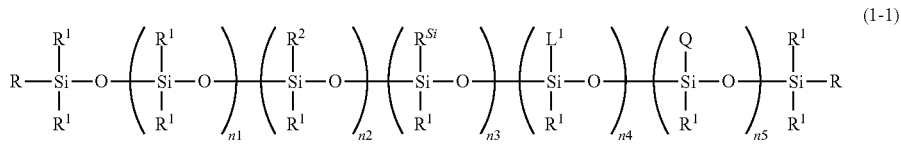
(1-1)

{wherein $R^1$, $R^2$, $R^{Si}$, $L^1$, and Q are synonymous with the groups described above; and R is a group selected from $R^1$, $R^2$, $R^{Si}$, $L^1$, and Q. (n1+n2+n3+n4+n5) is a number in a range of 201 to 1200; n1 is a number in a range of 100 to 1000; n2 is a number in a range of 0 to 500; n3 is a number in a range of 0 to 100; n4 is a number in a range of 0 to 100; and n5 is a number in a range of 0 to 100. However, when n2=0, at least one R moiety is $R^2$, and when n5=0, at least one R moiety is Q.}

The ratio occupied by the monovalent hydrocarbon group in the molecule of the diglycerin derivative-modified silicone of the present invention is preferably at most 50 mass % and more preferably at least 15 mass % and at most 40 mass %. Further, it is also possible to use a combination of two or more types of substances with different ratios occupied by the monovalent hydrocarbon groups in the molecule of the diglycerin derivative-modified silicone of the present invention in accordance with the type of oil agent.

A second aspect of the present invention is a composition containing the (A) diglycerin derivative-modified silicone described above.

The (A) diglycerin derivative-modified silicone described above may be a mixture of the following:

(A1) a high-molecular-weight diglycerin derivative-modified silicone with a number average molecular weight of at least 20,000 comprising: a halogen atom-substituted or unsubstituted monovalent hydrocarbon group having from 9 to 30 carbon atoms in a molecule; and as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %; and (A2) a low-molecular-weight diglycerin derivative-modified silicone with a number average molecular weight of less than 20,000 having a halogen atom-substituted or unsubstituted monovalent hydrocarbon group having from 9 to 30 carbon atoms in a molecule and having as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %.

The composition of the present invention may be one or more functional materials selected from the group consisting of surfactants, dispersants, and thickening agents. The composition may be used as a thickening emulsifier for a water-in-oil emulsion or a polyol-in-oil emulsion, in particular.

The composition of the present invention may further contain (B) water and/or (C) an oil agent.

The (C) oil agent is preferably a liquid at 5 to 100° C. and is preferably at least one type selected from the group consisting of volatile non-silicone oils, volatile silicone oils, nonvolatile non-silicone oils, and nonvolatile silicone oils.

The composition of the present invention may further contain (D) a film-forming agent (however, excluding agents falling under the category of component (A)).

The (D) film-forming agent is preferably at least one type selected from the group consisting of silicone resins, acryl silicone dendrimer copolymers, polyamide-modified silicones, alkyl-modified silicone waxes, alkyl-modified silicone resin waxes, organic film-forming polymers, and non-aqueous or aqueous dispersions of film-forming polymers.

The composition of the present invention may further contain at least one type selected from the group consisting of (E) a powder or coloring agent, (K) an ultraviolet light blocking component, and (N) a bioactive component.

The composition of the present invention may further contain (G) a polyol.

The composition of the present invention is preferably in the form of a water-in-oil emulsion or a polyol-in-oil emulsion.

One or more components selected from the components (D), (E), (K), and (N) are preferably present in one or more phases or interfaces selected from the group consisting of oil, water, and a polyol.

The composition of the present invention preferably does not contain a compound having an oxyalkylene structure having an average value of the number of repetitions of oxyalkylene units of two or more.

The present invention also relates to an external use preparation or cosmetic composition containing the composition described above.

The external use preparation or cosmetic composition of the present invention is preferably in the form of a water-in-oil emulsion or a polyol-in-oil emulsion.

The external use preparation or cosmetic composition of the present invention preferably does not contain a compound having an oxyalkylene structure having an average value of the number of repetitions of oxyalkylene units of two or more.

Advantageous Effects of Invention

The glycerin-modified silicone of the present invention itself has an excellent emulsification/dispersion performance and thickening effect, particularly in a composition in which the oil phase is a continuous phase. Therefore, it is possible to provide a composition which minutely and stably emulsifies and disperses an aqueous (or polyol) phase, is capable of forming an emulsion having high viscosity, and stable even when stored for a long period of time at high temperature, not only when the oil phase comprises a silicone oil or a mixed oil of a silicone oil and a non-silicone oil (ester-based oil or the like), but also when the oil phase primarily consists of a non-polar organic oil such as a mineral oil or isohexadecane, which has been difficult with conventional glycerin-modified silicones.

In addition, the composition of the present invention is essentially capable of overcoming problems associated with the oxidative degradation of polyoxyethylene (PEG), is stable over time at high temperature regardless of the type of the oil phase, and is capable of forming an emulsion having high viscosity.

That is, in the composition of the present invention, the diglycerin derivative-modified silicone has outstanding emulsification performance when used alone, which enables formulations in which compositions containing various oil agents do not contain compounds having a polyoxyethylene (PEG) structure. Therefore, it is possible to essentially overcome problems associated with the oxidative degradation of polyoxyethylene (PEG). The composition of the present invention may be used as a surfactant, a thickening agent, or a thickening emulsifier having the functions of both agents, and it may also be used as an external use preparation or a cosmetic composition.

In particular, with the present invention, by using a high-molecular-weight diglycerin derivative-modified silicone having a number average molecular weight of at least 20,000 and a low-molecular-weight diglycerin derivative-modified silicone having a number average molecular weight of less than 20,000 in combination at a desired ratio, in the case of a water (or polyol)-in-oil emulsion, it is possible to optionally and easily control the viscosity of the water (or polyol)-in-oil emulsion.

Further, with the present invention, it is possible to exhibit the tactile sensation improving effect of the composition by using a diglycerin derivative-modified silicone, which makes it possible to provide a high-grade external use preparation or a cosmetic composition which has a soft and natural tactile sensation while having a high viscosity, is smooth and light with good spread, and has an excellent moisturizing feel.

DESCRIPTION OF EMBODIMENTS

First, the diglycerin derivative-modified silicone of the present invention will be described in detail hereinafter.

[Diglycerin Derivative-Modified Silicone]The diglycerin derivative-modified silicone of the present invention contains as a lipophilic group a long-chain monovalent hydrocarbon group (preferably a long-chain alkyl group) in a molecule, has as a hydrophilic group only a glycerin derivative group not having an oxyalkylene structure having an average value of the number of repetitions of oxyalkylene units of two or more and having an average value of the number of repetitions of glycerin units in a range of 1.5 to 2.4, and not having other hydrophilic groups in the molecule. That is, since the diglycerin derivative-modified silicone of the present invention contains a long-chain hydrocarbon group as a lipophilic group and contains only a diglycerin derivative group as a hydrophilic group in a molecule, the diglycerin derivative-modified silicone itself has outstanding emulsification performance in comparison to known (poly)glycerin-modified silicones, and it is thus possible to design formulations not containing compounds having a polyoxyethylene (PEG) structure. As a result, it is possible to essentially overcome problems associated with the oxidative degradation of polyoxyethylene (PEG).

A first feature of the diglycerin derivative-modified silicone of the present invention is that the diglycerin derivative-modified silicone contains a long-chain hydrocarbon group, primarily contains a diglycerin derivative group as a hydrophilic group in a molecule, and does not contain other hydrophilic groups or hydrophilic structures such as polyoxyalkylene groups in the molecule.

First, the long-chain hydrocarbon group in the molecule of the diglycerin derivative-modified silicone of the present invention will be described in detail. The diglycerin derivative-modified silicone of the present invention contains a halogen atom-substituted or unsubstituted monovalent hydrocarbon group having from 9 to 30 carbon atoms in the molecule thereof. As a result of this long-chain hydrocarbon group being introduced into the molecule together with a hydrophilic group primarily consisting of a diglycerin derivative group described above, the glycerin derivative-modified silicone of the present invention exhibits superior compatibility not only with silicone oils, but also with non-silicone oils having high alkyl group contents, which makes it possible to obtain emulsions and dispersions containing non-silicone oils having excellent thermal stability and stability over time, for example. As a result, the emulsification performance of the substance alone with respect to oil agents is dramatically improved in comparison to publicly known (poly)glycerin-modified silicones, and an emulsification performance high enough to enable the design of formulations not containing compounds having a polyoxyethylene (PEG) structure is thus realized.

The halogen atom-substituted or unsubstituted monovalent hydrocarbon group having from 9 to 30 carbon atoms is at least one type of long-chain monovalent hydrocarbon group and may have two or more types of monovalent hydrocarbon groups with different numbers of carbon atoms in the same molecule. Further, the structure thereof is selected from a straight-chain structure, a branched structure, and a partially branched structure. In the present invention, an unsubstituted straight chain monovalent hydrocarbon group is particularly preferably used. An unsubstituted monovalent hydrocarbon group can be, for example, an alkyl group, aryl group, or aralkyl group having from 9 to 30 carbon atoms, preferably from 10 to 24 carbon atoms, and more preferably from 14 to 20 carbon atoms. On the other hand, examples of the halogen atom-substituted monovalent hydrocarbon group include a perfluoroalkyl group having from 9 to 30 carbon atoms, preferably from 10 to 24 carbon atoms, and more preferably from 14 to 20 carbon atoms. This type of monovalent hydrocarbon group is particularly preferably an alkyl group having from 9 to 30 carbon atoms, and an example thereof is a group represented by the general formula —$(CH_2)_v$—$CH_3$ (v is a number in a range of 8 to 29, preferably from 9 to 23, and more preferably from 13 to 19). By having a long-chain monovalent hydrocarbon group having from 9 to 30 carbon atoms, the compatibility is improved with respect to non-silicone oils having large hydrocarbon group contents, and the emulsification performance of the diglycerin derivative-modified silicone of the present invention is further enhanced.

In the diglycerin derivative-modified silicone of the present invention, the ratio occupied by the halogen atom-substituted or unsubstituted monovalent hydrocarbon group having from 9 to 30 carbon atoms in a molecule is at least 0.5 mass %, preferably at least 1.0 mass %, more preferably from 1 to 55 mass %, even more preferably from 5 to 50 mass %, even more preferably from 10 to 45 mass %, and even more preferably from 15 to 40 mass %. By controlling the amount of the monovalent hydrocarbon group in this way, the diglycerin derivative-modified silicone of the present invention is able to exhibit excellent compatibility and emulsifiability with respect to not only silicone oils, but also nearly all oil agents including non-silicone oils such as mineral oils and vegetable oils. Here, by setting the ratio occupied by the monovalent hydrocarbon group in the entire molecule to a relatively small value, it is possible to prioritize compatibility, thickening properties, and emulsifiability with silicone oils. Moreover, by setting the ratio occupied by the monovalent hydrocarbon group in the entire molecule to a relatively large value, it is possible to prioritize compatibility, thickening properties, and emulsifiability with non-silicone oils. On the other hand, when an oil agent to be preferentially emulsified, dispersed, or thickened is a silicone oil or a mixed oil comprising a silicone oil and a non-silicone oil and is an oil agent primarily consisting of a silicone oil, it is effective to suppress the ratio occupied by the monovalent hydrocarbon group in the molecule of the diglycerin derivative-modified silicone of the present invention. The ratio is preferably at least 0.5 mass % and less than 15 mass %, more preferably at least 0.5 mass % and less than 10 mass %, and particularly preferably at least 0.5 mass % and less than 5.0 mass %.

The diglycerin derivative-modified silicone of the present invention has the aforementioned long-chain monovalent hydrocarbon group in the molecule, has as a hydrophilic group only a glycerin derivative group not having an oxyalkylene structure having an average value of the number of repetitions of oxyalkylene units of two or more and having an average value of the number of repetitions of glycerin units in a range of 1.5 to 2.4, and not having other hydrophilic groups in the molecule. Here, a hydrophilic group or a hydrophilic structure is a functional group or a molecular structure which imparts the property of hydrophilicity to the silicone molecule and is typically a functional group or structure derived from a hydrophilic compound.

In particular, in the present invention, it is necessary to satisfy the condition that the average value of the number of repetitions of glycerin units in a molecule falls within a range of 1.5 to 2.4. A glycerin derivative group that does not satisfy this condition is not preferable in that the emulsification performance is diminished. In addition, in the present invention, an oxyalkylene derivative group containing an oxyalkylene structure having an average number of repetitions of oxyalkylene units of two or more or a similar structure must not be present in the molecule as a hydrophilic group. In particular, when a polyoxyalkylene-modified group containing a polyoxyalkylene structure or a similar structure is present in the molecule as a hydrophilic group, the object of the present invention of essentially overcoming problems associated with the oxidative degradation of polyoxyethylene (PEG) cannot be achieved. In addition, when a polyoxyalkylene-modified group is contained, the oily feeling, stickiness, or the like of a cosmetic composition containing the substance—a water-in-oil emulsion cosmetic, in particular—cannot be suppressed. As a result, the tactile sensation thereof may be dramatically diminished in comparison to cases in which only a glycerin derivative group is contained as a hydrophilic group.

A second feature of the diglycerin derivative-modified silicone of the present invention is that the diglycerin derivative-modified silicone has a diglycerin derivative group as a hydrophilic group in the molecule. The average value of the number of repetitions of glycerin units of this diglycerin derivative group is in a range of 1.5 to 2.4, preferably in a range of 1.8 to 2.2, and most preferably 2 on average. When the average value of the number of repetitions of glycerin units is less than the aforementioned lower limit or greater than the aforementioned upper limit, the emulsification/dispersion performance of the glycerin derivative-modified silicone is diminished, and it becomes difficult to accommodate an oil phase containing an organic oil, in particular, which makes it impossible to obtain a composition—a water-in-oil emulsion composition, in particular—which is stable over a long period of time.

A diglycerin derivative group in which the number of glycerin unit repetitions, on average, is 2 is preferably contained in an amount exceeding 30 mass % of the total, relative to other glycerin derivative groups, more preferably not less than 50 mass %, and particularly preferably not less than 80 mass %. Most preferably, it is a pure product in which the purity of the diglycerin derivative groups exceeds 98 mass %. That is, the average value of the number of repetitions of glycerin units of the diglycerin derivative-modified silicone of the present invention is within the range described above, and a substance in which the number of repetitions is 2 may be the primary hydrophilic group, or a high-purity diglycerin portion alone may be the primary hydrophilic group. On the other hand, a mixture of glycerin derivative-modified silicones such as one prepared by mixing purified triglycerin derivative-modified silicone in which the number of repetitions of glycerin units is 3 and a monoglycerin derivative-modified silicone in which the number of repetitions of glycerin units is 1 at a substance ratio of 1:1 cannot be suitably used as the diglycerin derivative-modified silicone of the present invention since the emulsification/dispersion performance of each component is originally poor.

The diglycerin derivative group is preferably a diglycerin derivative group-containing organic group bonded to a silicon atom via a linking group that is at least divalent and preferably contains at least one type of glycerin unit selected from hydrophilic units represented by the following structural formulae (4-1) to (4-3), the number of repetitions thereof being in a range of 1.5 to 2.4 on average (however, the substance does not have an oxyalkylene structure having an average value of the number of repetitions of oxyalkylene units of two or more in the functional group). The preferred ranges of the number of glycerin unit repetitions are the same as described above.

[Formula 10]

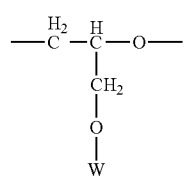

(4-1)

(wherein W is a hydrogen atom or an alkyl group having from 1 to 20 carbon atoms.)

[Formula 11]

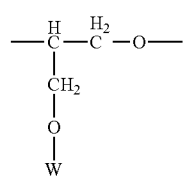

(4-2)

(wherein W is synonymous with the group described above.)

[Formula 12]

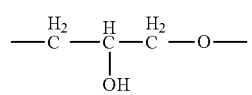

(4-3)

In formulae (4-1) to (4-3), W is a hydrogen atom or an alkyl group having from 1 to 20 carbon atoms, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The number of repetitions of glycerin units of the diglycerin derivative group is in a range of 1.5 to 2.4 on average and is more preferably 2 on average. The repeating structure of glycerin units preferably does not have branches, but it may have a partially branched structure in which a portion thereof is a polyglycerol group or a polyglycidyl ether group.

A divalent linking group is a divalent organic group which is a silicon atom bonding site contained in the diglycerin derivative group, the divalent organic group not containing an oxyalkylene structure having an average value of the number of repetitions of oxyalkylene units of two or more. Specific examples include straight-chain or branched-chain alkylene groups such as ethylene groups, propylene groups, butylene groups, and hexylene groups; alkylene phenylene groups such as ethylene phenylene groups and propylene phenylene groups; alkylene aralkylene groups such as ethylene benzylene groups; alkylenoxy phenylene groups such as ethylenoxy phenylene groups and propylenoxy phenylene groups; and alkylenoxy benzylene groups such as methylenoxy benzylene groups, ethylenoxy benzylene groups, and propylenoxy benzylene groups. A preferable example is a group selected from divalent organic groups represented by the following general formulae.

[Formula 13]

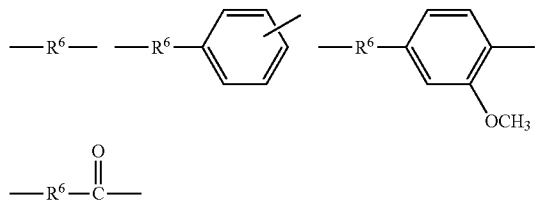

(In the formulae, $R^6$ may have a substituent and is each independently a straight-chain or branched-chain alkylene group or alkenylene group having from 2 to 22 carbon atoms or an arylene group having from 6 to 22 carbon atoms.)

The diglycerin derivative group is more preferably a diglycerin derivative group represented by the following structural formula (5):

(5)

In the formula, $R^5$ is a divalent organic group that does not have an oxyalkylene structure having an average number of repetitions of oxyalkylene units of two or more, examples of which include the same examples as those listed for the divalent linking group described above. X is at least one glycerin unit selected from hydrophilic units represented by the above structural formulae (4-1) to (4-3). m is the number of glycerin unit repetitions, and on average, is a number in a range of 1.5 to 2.4. The preferred ranges of the number of glycerin unit repetitions are the same as described above.

Most preferably, the diglycerin derivative group-containing organic group is a diglycerin derivative group-containing organic group represented by following general formula (5-1):

[Formula 14]

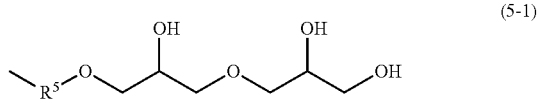

(5-1)

(wherein $R^5$ is a divalent organic group that does not have an oxyalkylene structure having an average value of the number of repetitions of oxyalkylene units of two or more) or the following general formula (5-2):

[Formula 15]

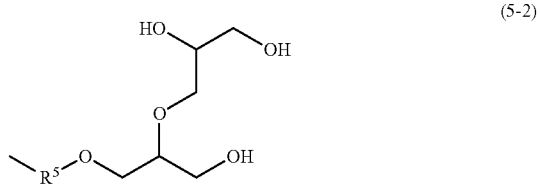

(5-2)

(wherein $R^5$ is synonymous with those described above.)

In the diglycerin derivative-modified silicone of the present invention, the diglycerin derivative group-containing organic group is preferably a hydrophilic group derived from diglycerin monoallyl ether or diglyceryl eugenol.

The bond position of the diglycerin derivative-containing organic group can be either the terminal or side chain of polysiloxane, which is the main chain; and the structure may have two or more diglycerin derivative-containing organic groups in the molecule of diglycerin derivative-modified silicone. Further, these two or more diglycerin derivative-containing organic groups can be structured such that bonding occurs only in a side chain of polysiloxane, which is the main chain, only at a terminal, or in a side chain and at a terminal.

The polysiloxane main chain of the diglycerin derivative-modified silicone of the present invention, which has the long-chain monovalent hydrocarbon group described above and only a diglycerin derivative-containing organic group as a hydrophilic group, may have a straight-chain structure, a branched-chain structure, or a silicone resin structure. As long as it does not conflict with the object of the present invention, it may be a diglycerin derivative-modified silicone which is further modified by an organic group other than a long-chain monovalent hydrocarbon group or a hydrophilic group, examples of which include organic groups such as alkoxy groups, (meth)acryl groups, epoxy groups, acyl groups, ester groups, mercapto groups, carbonyl groups, and ether bond-containing groups (including combinations of the functional groups described above) It is preferably a co-modified diglycerin derivative-modified silicone represented by the following general formula (1).

General Formula (1)

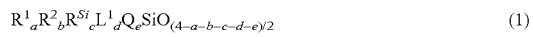

(1)

{In the general formula (1), $R^1$ is a halogen atom-substituted or unsubstituted monovalent hydrocarbon group having from 1 to 8 carbon atoms, an alkoxy group, a hydrogen atom, or a hydroxyl group.

$R^2$ is a halogen atom-substituted or unsubstituted monovalent hydrocarbon group having from 9 to 30 carbon atoms.

$R^{Si}$ is a chain organosiloxane group represented by the following general formula (2-1):

[Formula 16]

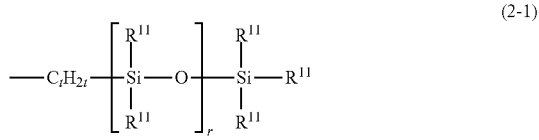

(2-1)

(wherein $R^{11}$ is a halogen atom-substituted or unsubstituted monovalent hydrocarbon group having from 1 to 30 carbon atoms, a hydroxyl group, or a hydrogen atom, and at least one of the $R^{11}$ moieties is the monovalent hydrocarbon group; t is a number in a range of 2 to 10; and r is a number in a range of 1 to 500); or the general formula (2-2) below:

[Formula 17]

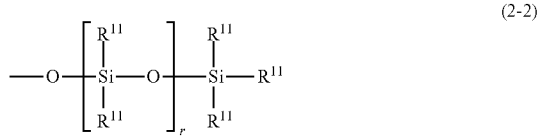

(2-2)

(wherein $R^{11}$ and r are synonymous with those described above).
$L^1$ represents a silylalkyl group having the siloxane dendron structure represented by the following general formula (3) when i=1;

[Formula 18]

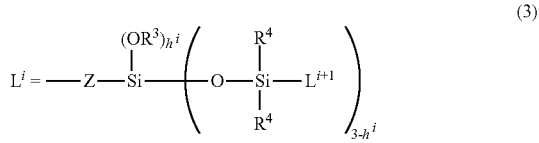

(3)

(wherein $R^3$ is a halogen atom-substituted or unsubstituted, straight-chain or branched monovalent hydrocarbon group having from 1 to 30 carbon atoms; $R^4$ is each independently an alkyl group or phenyl group having from 1 to 6 carbon atoms; Z is a divalent organic group; i is the generation of the silylalkyl group represented by Li and is an integer of 1 to k when k is a number of generations serving as a number of repetitions of the silylalkyl group; the number of generations k is an integer from 1 to 10; Li+1 is the silylalkyl group when i is less than k, and $R^4$ when i=k; and $h^i$ is a number in a range of 0 to 3);
Q is a glycerin derivative group having an average value of the number of repetitions of glycerin units in a range of 1.5 to 2.4; and
a, b, c, d, and e are numbers in ranges so that $0 \leq a \leq 2.5$, $0 < b \leq 1.5$, $0 \leq c+d \leq 1.5$, and $0.001 \leq e \leq 1.5$.}
In the diglycerin derivative-modified silicone of the present invention represented by general formula (1), the long-chain monovalent hydrocarbon group represented by $R^2$ is an essential substituent, and b is a number which is greater than 0 and is in a range so that $0 < b \leq 1.5$. In particular, from the perspective of improving the emulsifiability with respect to non-silicone oil agents, b is preferably in a range so that $0.0001 \leq b \leq 1.5$ and more preferably in a range so that $0.001 \leq b \leq 1.5$.

Similarly, the diglycerin derivative-modified silicone of the present invention may have a chain organosiloxane group represented by $R^{Si}$ and/or a silylalkyl group having a siloxane dendron structure represented by $L^1$. By having these functional groups, these functional groups in the diglycerin derivative-modified silicone of the present invention may be any functional groups, wherein c+d is a number greater than or equal to 0. On the other hand, when these functional groups are present in the molecule, it is preferable for c+d to be a number greater than 0 and in a range so that $0.0001 \leq c+d \leq 1.5$, and more preferably $0.001 \leq c+d \leq 1.5$.

At this time, in addition to satisfying the relation $0.001 \leq c+d \leq 1.5$, the suitable values of c and d are represented as follows by essential functional groups in the molecule.
(1) When there is a group represented by $R^{Si}$: $0.001 \leq c \leq 1.5$ and $0 \leq d \leq 1.5$.
(2) When there is a group represented by $L^1$: $0 \leq c \leq 1.5$ and $0.001 \leq d \leq 1.5$.
(3) When there are both a group represented by $R^{Si}$ and a group represented by $L^1$: $0.001 \leq c \leq 1.5$ and $0.001 \leq d \leq 1.5$.

In general formula (1), $R^1$ is halogen atom-substituted or unsubstituted monovalent hydrocarbon group having from 1 to 8 carbon atoms, an alkoxy group, a hydrogen atom, or a hydroxyl group.

Examples of a monovalent hydrocarbon group having from 1 to 8 carbon atoms include alkyl groups such as methyl groups, ethyl groups, propyl groups, butyl groups, pentyl groups, hexyl groups, heptyl groups, and octyl groups; cycloalkyl groups such as cyclopentyl groups and cyclohexyl groups; alkenyl groups such as vinyl groups allyl groups, and butenyl groups; aryl groups such as phenyl groups and tolyl groups; aralkyl groups such as benzyl groups and phenethyl groups; and groups in which the hydrogen atoms bonded to the carbon atoms of these groups are substituted at least partially by halogen atoms such as fluorine atoms (however, the total number of carbon atoms is from 1 to 8). The monovalent hydrocarbon group is preferably a group other than an alkenyl group, and is particularly preferably a methyl group, an ethyl group, or a phenyl group. In addition, examples alkoxy groups include methoxy groups, ethoxy groups, isopropanoxy groups, and higher alkoxy groups.

Particularly, the $R^1$ moieties are preferably monovalent hydrocarbon groups having from 1 to 8 carbon atoms and that are free of unsaturated aliphatic bonds or monovalent fluorinated hydrocarbon groups. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is a methyl group, an ethyl group, or a phenyl group, and more preferably from 90 mol % to 100 mol % of all the $R^1$ moieties are selected from methyl groups, ethyl groups, or phenyl groups.

When $R^2$ in general formula (1) is a halogen atom-substituted or unsubstituted monovalent hydrocarbon group having from 9 to 30 carbon atoms and has a long-chain monovalent hydrocarbon group having from 9 to 30 carbon atoms, the compatibility is improved with respect to non-silicone oils having large hydrocarbon group contents, and the emulsification performance of the diglycerin derivative-modified silicone of the present invention is further enhanced. More specifically, an unsubstituted straight-chain monovalent hydrocarbon group is preferably used for $R^2$. An unsubstituted monovalent hydrocarbon group may be, for example, an alkyl group, aryl group, or aralkyl group having from 9 to 30 carbon atoms, preferably from 10 to 24 carbon atoms, and more preferably from 14 to 20 carbon atoms. On the other hand, examples of the halogen atom-substituted monovalent hydrocarbon group include perfluoroalkyl groups having from 9 to 30 carbon atoms, preferably from 10 to 24 carbon atoms, and more preferably from 14 to 20 carbon atoms. Such a monovalent hydrocarbon group is particularly preferably an alkyl group having from 9 to 30 carbon atoms, examples of which include straight-chain or branched-chain groups represented by the general formula —$(CH_2)_v$—$CH_3$ (v is a number in a range of 8 to 29, preferably from 9 to 23, and more preferably from 13 to 19). In particular, examples of $R^2$ include alkyl groups such as nonyl groups, decyl groups, undecyl groups, dodecyl groups, tridecyl groups, tetradecyl groups, pentadecyl groups, hexadecyl groups, heptadecyl groups, stearyl groups (octadecyl groups), nonadecyl groups, icosyl groups, henicosyl groups, docosyl groups, tricosyl groups, tetracosyl groups, myristoleyl groups, palmitoleyl groups, oleyl groups, linoyl groups, linoleyl groups, ricinoleyl groups, and isostearyl groups and aralkyl groups such as methyl phenyethyl groups and phenyl benzyl groups.

The group represented by $R^{Si}$ in general formula (1) is a chain organosiloxane group represented by general formula (2-1) or (2-2) above. By introducing this group at the main chain and/or side chain of polysiloxane, it is possible to adjust the affinity or dispersion stability with respect to various components such as oil agents and powders incorporated into an external use preparation or a cosmetic composition, as well as the sensation during use. In particular, having a chain organopolysiloxane group represented by $R^{Si}$ in the molecule is useful in that the compatibility and compounding stability with respect to silicone oils is further improved.

The chain organosiloxane group in general formula (2-1) or (2-2) has a straight polysiloxane chain structure, unlike a silylalkyl group, which has a siloxane dendron structure. In general formula (2-1) or (2-2), $R^{11}$ are each independently a halogen atom-substituted or unsubstituted monovalent hydrocarbon group having from 1 to 30 carbon atoms, a hydroxyl group, or a hydrogen atom. The halogen atom-substituted or unsubstituted monovalent hydrocarbon group having from 1 to 30 carbon atoms is preferably an alkyl group having from 1 to 30 carbon atoms, an aryl group having from 6 to 30 carbon atoms, an aralkyl group having from 6 to 30 carbon atoms, or a cycloalkyl group having from 6 to 30 carbon atoms, examples of which include alkyl groups such as methyl groups, ethyl groups, propyl groups, butyl groups, pentyl groups, hexyl groups, heptyl groups, octyl groups, and decyl groups; cycloalkyl groups such as cyclopentyl groups and cyclohexyl groups; and aryl groups such as phenyl groups and tolyl groups. The hydrogen atoms bonded to the carbon atoms of these groups may be substituted at least partially by halogen atoms such as fluorine. A methyl group, a phenyl group, or a hydroxyl group is particularly preferable as $R^{11}$. A configuration in which a part of $R^{11}$ is a methyl group and another part of $R^{11}$ is a long chain alkyl group having from 8 to 30 carbon atoms is also preferable.

In general formula (2-1) or (2-2), t is a number in a range of 2 to 10; r is a number in a range of 1 to 500; and r preferably is a number in a range of 2 to 500. Such a straight chain organosiloxane group is hydrophobic. From the perspective of compatibility with various oil agents, r preferably is a number in a range of 1 to 100, and particularly preferably is a number in a range of 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external use preparation or cosmetic composition that incorporates the diglycerin derivative-modified silicone is used, the silylalkyl group inhibits an unpleasant sticky feeling, has excellent smoothness, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the halogen atom-substituted or unsubstituted, straight-chain or branched monovalent hydrocarbon group having from 1 to 30 carbon atoms represented by $R^3$ in general formula (3) include alkyl groups such as methyl groups, ethyl groups, propyl groups, butyl groups, pentyl groups, hexyl groups, heptyl groups, and octyl groups; cycloalkyl groups such as cyclopentyl groups and cyclohexyl groups; alkenyl groups such as vinyl groups, allyl groups, and butenyl groups; aryl groups such as phenyl groups and tolyl groups; aralkyl groups such as benzyl groups; and groups wherein the hydrogen atoms bonded to the carbon atoms of these groups are substituted at least partially by halogen atoms such as fluorine.

Among the phenyl group or the alkyl group having from 1 to 6 carbon atoms represented by $R^4$ in general formula (3), examples of the alkyl group having from 1 to 6 carbon atoms include methyl, ethyl, n-propyl, i-propyl, n-butyl, i-butyl, s-butyl, pentyl, neopentyl, cyclopentyl, hexyl, and similar straight-chain, branched, or cyclic alkyl groups.

In the general formula (3), in the case of i=k, $R^4$ is preferably a methyl group or a phenyl group. In particular, $R^4$ is preferably a methyl group when i=k.

From an industrial standpoint, the number of generations k is preferably an integer of 1 to 3, and more preferably is 1 or 2. In each of the number of generations, the group represented by $L^1$ represented as follows. In the formulae, $R^3$, $R^4$, and Z are the same groups as described above.

When the number of generations is k=1, $L^1$ is represented by the following general formula (3-1).

[Formula 19]

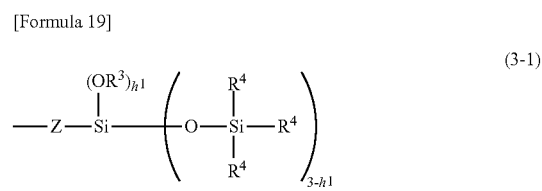

(3-1)

When the number of generations is k=2, $L^1$ is represented by the following general formula (3-2).

[Formula 20]

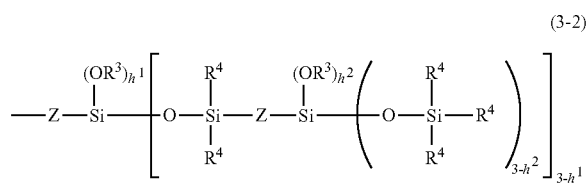
(3-2)

When the number of generations is k=3, $L^1$ is represented by the following general formula (3-3).

[Formula 21]

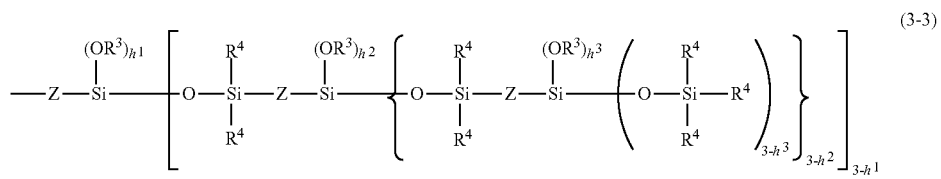
(3-3)

In the structures represented by the general formulae (3-1) to (3-3) in the case of the number of generations is from 1 to 3, each of $h^1$, $h^2$ and $h^3$ moieties is independently a number in a range of 0 to 3. These $h^i$ moieties are preferably a number in a range of 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. However, in the present invention, a group containing an oxyalkylene structure having an average number of repetitions of oxyalkylene units of two or more cannot be used and is not preferable.

Preferably, Z are each independently a group selected from divalent organic groups represented by the following general formula.

[Formula 22]

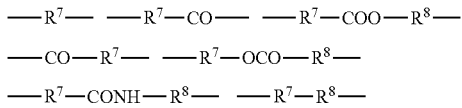

Of these, Z in $L^1$ is preferably a divalent organic group represented by general formula —$R^7$— that is introduced by a reaction between a silicon-bonded hydrogen atom and an alkenyl group. Likewise, Z is preferably a divalent organic group represented by general formula —$R^7$—COO—$R^8$— that is introduced by a reaction between a silicon-bonded hydrogen atom and an unsaturated carboxylic ester group.

On the other hand, in the silylalkyl group represented by $L^i$, in which the number of generations k is not less than 2, and $L^i$ is $L^2$ to $L^k$, Z is preferably an alkylene group having from 2 to 10 carbon atoms and, in particular, is preferably a group selected from an ethylene group, a propylene group, a methylethylene group, and a hexylene group, and most preferably is an ethylene group.

In the general formula described above, $R^7$ are each independently a substituted or unsubstituted straight-chain or branched chain alkylene group or alkenylene group having from 2 to 22 carbon atoms or an arylene group having from 6 to 22 carbon atoms. More specifically, examples of $R^7$ include an ethylene group, a propylene group, a butylene group, a hexylene group, and similar straight-chain alkylene groups; a methylmethylene group, a methylethylene group, a 1-methylpentylene group, a 1,4-dimethylbutylene group, and similar branched alkylene groups. $R^7$ is preferably a group selected from an ethylene group, a propylene group, a methylethylene group, and a hexylene group.

In the general formula described above, $R^8$ is a group selected from divalent organic groups represented by the following formula.

[Formula 23]

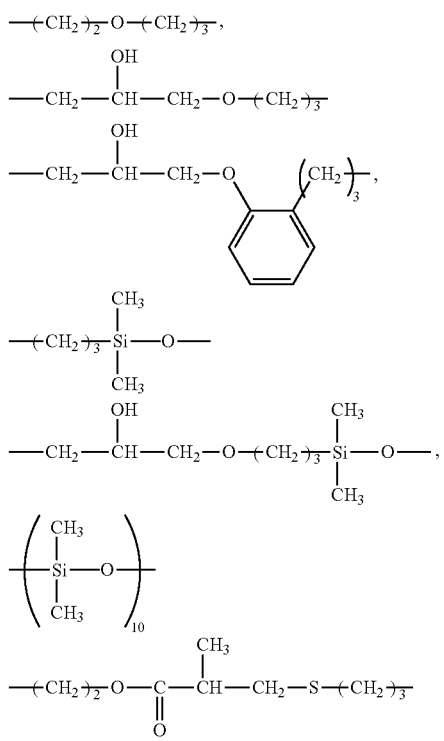

In general formula (1), Q is a glycerin derivative group having an average value of the number of repetitions of glycerin units in a range of 1.5 to 2.4, examples of which are the hydrophilic groups described above, which are groups constituting the hydrophilic sites of the diglycerin derivative-modified silicone, and the group is selected appropriately.

The diglycerin derivative-modified silicone of the present invention is particularly preferably a diglycerin derivative-modified silicone having a straight-chain polysiloxane structure represented by the following structural formula (1-1):

[Formula 24]

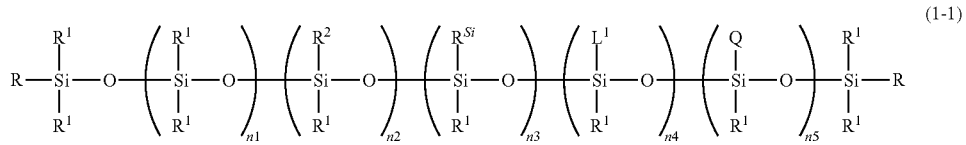

(1-1)

{wherein $R^1$, $R^2$, $R^{Si}$, $L^i$, and Q are synonymous with the groups described above; and R is a group selected from $R^1$, $R^2$, $R^{Si}$, $L^i$, and Q. (n1+n2+n3+n4+n5) is a number in a range of 1 to 1200; n1 is a number in a range of 0 to 1000; n2 is a number in a range of 0 to 500; n3 is a number in a range of 0 to 100; n4 is a number in a range of 0 to 100; and n5 is a number in a range of 0 to 100. However, when n2=0, at least one R moiety is $R^2$, and when n5=0, at least one R moiety is Q.}. The diglycerin derivative-modified silicone is particularly preferably a diglycerin derivative-modified silicone having a straight-chain polymethyl siloxane structure represented by the following structural formula (1-1A), wherein all of the $R^1$ moieties are methyl groups.

[Formula 25]

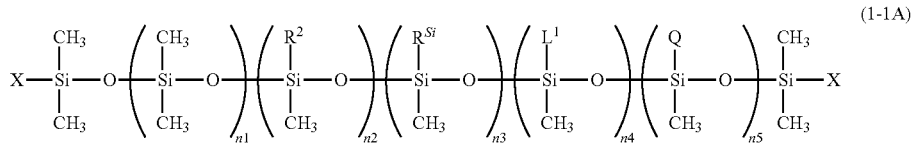

(1-1A)

In the formula,
$R^2$, $R^{Si}$, $L^1$, and Q are each independently synonymous with those described above;
X is a group selected from the group consisting of a methyl group, $R^2$, $R^{Si}$, $L^1$, and Q;
n1, n2, n3, n4, and n5 are numbers so that (n1+n2+n3+n4+n5) is in a range of 1 to 1200;
n1 is a number in a range of 0 to 1000; n2 is a number in a range of 0 to 500; n3 is a number in a range of 0 to 100; n4 is a number in a range of 0 to 100; and n5 is a number in a range of 0 to 100. However, when n2=0, at least one of the X moieties is $R^2$, and when n=5, at least one of the X moieties is Q).

In formula (1-1) or formula (1-1A), (n1+n2+n3+n4+n5) is in a range of 1 to 1200, and the silicone may be a diglycerin derivative-modified silicone having a relatively low degree of polymerization and having a small molecular weight silicone, wherein the number of siloxane units is from 1 to 200. On the other hand, using a high-molecular-weight diglycerin derivative-modified silicone is advantageous in that, when the composition containing the diglycerin derivative-modified silicone of the present invention is in the form of an emulsion, it is possible to stably emulsify the composition and to maintain the viscosity thereof at a high level.

Such a high-molecular-weight diglycerin derivative-modified silicone is particularly preferably such that (n1+n2+n3+n4+n5) is a number in a range of 201 to 1200 in formula (1-1) or formula (1-1A).

Here, (n1+n2+n3+n4+n5) is more preferably a number in a range of 201 to 1000 and particularly preferably in a range of 201 to 800 from the perspective of the emulsification performance or thickening properties when used as an emulsifier or a thickening agent/gelling agent for a water-in-oil emulsion. Similarly, n1 is a number in a range of 100 to 1000, more preferably a range of 100 to 700, and even more preferably a range of 100 to 600. Here, n2 is a number in a range of 0 to 500, more preferably a range of 1 to 500, and even more preferably a range of 1 to 300. In addition, n3 is preferably a number in a range of 0 to 100 and more preferably a range of 0 to 50. Further, n4 is preferably a number in a range of 0 to 100 and more preferably a range of 1 to 50. In addition, n5 is preferably a number in a range of 0 to 100 and more preferably a range of 1 to 50.

When $R^2$ is the long-chain monovalent hydrocarbon group and in particular an alkyl group, n2 is particularly preferably such that n2>1, and n2 is preferably in a range of 1 to 300 from the perspective of surface activity and compatibility with oil agents other than silicone.

Here, n4 preferably is a number in a range of 0 to 100, and it is particularly preferable that n4>1 and that it has least one silylalkyl group (-$L^1$) having a siloxane dendron structure in a side chain portion, while n4 is preferably in a range of 1 to 50.

In addition, n5 is a number in a range of 0 to 100 and is preferably in a number in a range of 1 to 50. However, when n5=0, at least one of the X moieties must be Q.

In the above structural formula (1-1A), Q is a glycerin derivative group having an average value of the number of repetitions of glycerin units in a range of 1.5 to 2.4, examples of which are the hydrophilic groups described above, and the group is selected appropriately.

Furthermore, the diglycerin derivative-modified silicone may be a mixture of one or two or more types of diglycerin derivative-modified silicone represented by general formula (1). More specifically, the diglycerin derivative-modified silicone may be a mixture of at least two types of diglycerin derivative-modified silicone, with different types of modified groups, modification rates, and degrees of polymerization of the siloxane main chain.

The diglycerin derivative-modified silicone is more preferably a diglycerin derivative-modified silicone represented by the following structural formula (1-1-1):

[Formula 26]

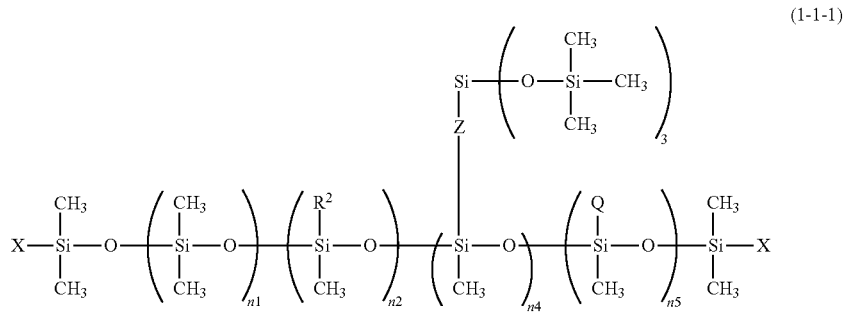

(wherein
$R^2$, Q, X, Z, n1, n2, n4, and n5 are synonymous with those described above), or the following structural formula (1-1-2):

[Formula 27]

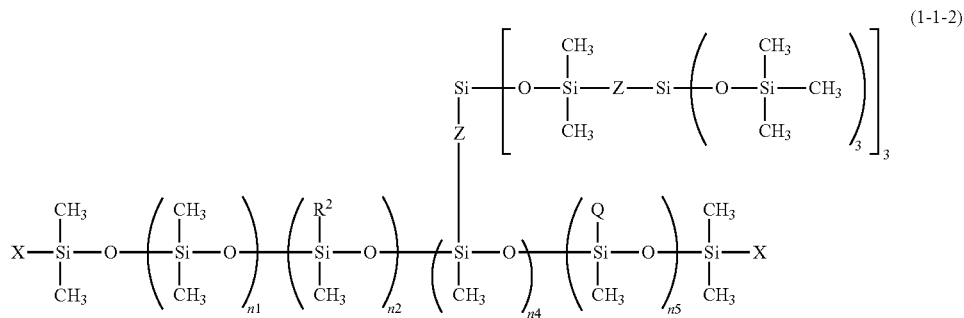

(wherein
$R^2$, Q, X, Z, n1, n2, n4, and n5 are synonymous with those described above).

When considering applications of an emulsifier for a water-in-oil emulsion or a powder-in-oil dispersant, the modification rate of organopolysiloxane due to the diglycerin derivative-containing organic group is preferably in a range of 0.001 to 15 mol %, more preferably within a range of 0.01 to 10 mol %, and even more preferably within the range from 0.1 to 5 mol % of all functional groups bonded to polysiloxane, which is the main chain. Furthermore, in the glycerin derivative-modified silicone represented by structural formula (1-1), the modification rate (mol %) resulting from the glycerin derivative-containing organic group is represented by the following formula:

Modification rate(mol %)=(number of diglycerin derivative-containing organic groups bonded to silicon atoms per molecule)/{6+2×(n1+n2+n3+n4)}×100

For example, in the case of a diglycerin derivative-modified silicone comprising trisiloxane having one diglycerin derivative-containing organic group, 1 of the 8 silicon-bonded functional groups is modified by the diglycerin derivative-containing organic group, so the modification rate by the diglycerin derivative-containing organic group is 12.5 mol %.

The diglycerin derivative-modified silicone of the present invention may be a high-molecular-weight substance having a number average molecular weight of at least 20,000. The number of repetitions of siloxane units of such a high-molecular-weight diglycerin derivative-modified silicone is preferably at least 100, more preferably at least 200, and even more preferably at least 300. By using a high-molecular-weight diglycerin derivative-modified silicone, when the composition containing the diglycerin derivative-modified silicone of the present invention is in the form of an emulsion, it is possible to stably emulsify the composition and to maintain the viscosity thereof at a high level. The number average molecular weight of the diglycerin derivative-modified silicone of the present invention can be easily specified using nuclear magnetic resonance analysis (nuclear species 29Si, 13C, and 1H) or the like, but when synthesizing the substance using an organohydrogenpolysiloxane having silicon-bonded hydrogen atoms by means of a hydrosilylation reaction as a starting substance, the number average molecular weight of the organohydrogenpolysiloxane (methylhydrogenpolysiloxane or the like) serving as a raw material can be identified by nuclear magnetic resonance analysis (nuclear species 29Si or the like) in advance, and the theoretical value of the number average molecular weight can also be calculated from the value of the molecular weight and the introduction rate of modified groups introduced by the hydrosilylation reaction.

{Synthesis of Diglycerin Derivative-Modified Silicone}

The diglycerin derivative-modified silicone can be obtained by, for example, reacting (a1) a glycerin derivative having one reactive unsaturated group per molecule, (b1) organopolysiloxane having silicon-bonded hydrogen atoms, and (c1) a long-chain hydrocarbon compound having one reactive unsaturated group per molecule, and if necessary, (d1) a siloxane dendron compound having one reactive unsaturated group per molecule, and/or (e1) a chain organopolysiloxane compound having one reactive unsaturated group per molecule in the presence of a hydrosilylation reaction catalyst. The reactive unsaturated group is preferably an unsaturated functional group having a carbon-carbon double bond, an example of which is an alkenyl group or unsaturated carboxylic acid ester group. In this case, the —$R^1$ group can be considered to be contained in component (b1), and —$R^2$ is introduced by the component (c1), while -$L^1$ is introduced by component (d1). Furthermore, at this time, by using an excessive amount of component (a1) for the silicon-bonded hydrogen atoms in component (b1), it is possible to obtain a glycerin derivative-modified silicone.

More specifically, the diglycerin derivative-modified silicone can be obtained as follows, for example.

The diglycerin derivative-modified silicone can be obtained by an addition reaction of organopolysiloxane having a silicon-hydrogen bond, and an unsaturated long-chain hydrocarbon compound having a carbon-carbon double bond at one terminal of the molecular chain and an unsaturated ether compound of a diglycerin derivative having a carbon-carbon double bond in the molecule. Furthermore, a siloxane dendron compound having a carbon-carbon double bond at one terminal of the molecular chain and/or a chain organopolysiloxane having a carbon-carbon double bond at one terminal of the molecular chain may be further addition-reacted. In addition, an unsaturated short-chain hydrocarbon compound having a carbon-carbon double bond at one end of the molecular chain (halogen atom-substituted or unsubstituted) may be further reacted as necessary.

In the above case, the diglycerin derivative-modified silicone can be obtained as the product of a hydrosilylation reaction between the unsaturated long-chain hydrocarbon compound and an unsaturated ether compound of the diglycerin derivative, and optionally the siloxane dendron compound, and/or a chain organopolysiloxane having a carbon-carbon double bond at one terminal of the molecular chain and a SiH group-containing siloxane. This enables the introduction of a long-chain hydrocarbon group and a diglycerin derivative group-containing organic group, and optionally a silylalkyl group having a siloxane dendron structure, and/or a chain organopolysiloxane group, and/or a short-chain hydrocarbon group into the polysiloxane chain of the diglycerin derivative-modified silicone. This reaction can be performed as a batch or can take the form of successive reactions. However, successive reactions are preferable from the perspectives of safety and quality control.

For example, the glycerin derivative-modified silicone can be obtained by reacting at least the (b2) organohydrogensiloxane represented by the following formula (1'), (a2) a diglycerin derivative having one reactive unsaturated group per molecule, and (c2) a long-chain hydrocarbon compound having at least one reactive unsaturated group per molecule in the presence of a hydrosilylation reaction catalyst.

(wherein $R^1$, a, b, c, d and e are synonymous with those described above). It is preferable to further react (d) a siloxane dendron compound having one reactive unsaturated group per molecule, and/or (e) a chain organopolysiloxane having one reactive unsaturated group per molecule.

The diglycerin derivative-modified silicone can be preferably produced by reacting together component (a2), component (c2), and/or component (d) and/or component (e), as well as (b2) the organohydrogensiloxane represented by general formula (1'), or by successively addition-reacting the (b2) organohydrogensiloxane and optionally the component (d) and/or the component (e), addition-reacting the component (c2), and further addition-reacting the component (a2), in a state in which (a1) a diglycerin derivative having one reactive unsaturated group per molecule, (c1) a long-chain hydrocarbon compound having one reactive unsaturated group per molecule, and optionally (d) a siloxane dendron compound having one reactive unsaturated group per molecule, and/or (e) a chain organopolysiloxane having one reactive unsaturated group per molecule coexist.

The (b2) organohydrogensiloxane used in the synthesis of the diglycerin derivative-modified silicone is preferably an organohydrogensiloxane represented by, for example, the following structural formula (1-1)':

[Formula 28]

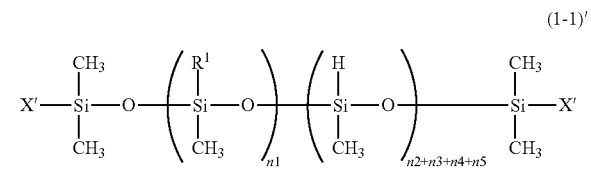

(wherein $R^1$ are each independently synonymous with that described above;

X' is a group selected from $R^1$ or hydrogen atom; and n1, n2, n3, n4, and n5 are synonymous with those described above; however, when n2+n3+n4+n5=0, at least one of the X' moieties is a hydrogen atom.)

The diglycerin derivative-modified silicone is preferably synthesized by performing a hydrosilylation reaction on (a) a diglycerin derivative having a carbon-carbon double bond at a terminal of the molecular chain, (c) a long-chain hydrocarbon compound having one reactive unsaturated group per molecule, and (b) an organohydrogenpolysiloxane. At this time, the organohydrogensiloxane serving as component (b) is preferably an organohydrogensiloxane obtained by adding the component (d1) and/or the component (e1) by means of successive addition reactions. In this case, the organohydrogensiloxane immediately prior to reaction with component (a) (after successive reactions with other components) is preferably represented by the following structural formula (1-1A').

[Formula 29]

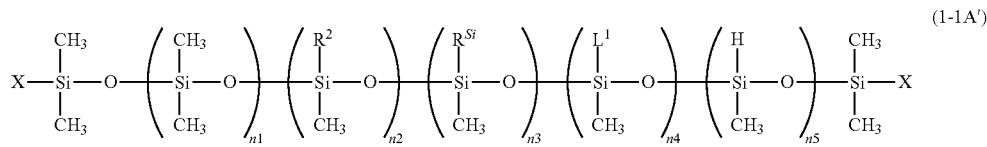

(1-1A')

(wherein

R² and L¹ are each independently synonymous with those described above;

X is selected from the group consisting of a methyl group, R², L¹, and a hydrogen atom (H);

n1, n2, n3, n4, and n5 are numbers so that (n1+n2+n3+n4+n5) is in a range of 1 to 1200;

n1 is a number in a range of 0 to 1000; n2 is a number in a range of 0 to 500; n3 is a number in a range of 0 to 100; n4 is a number in a range of 0 to 100; and n5 is a number in a range of 0 to 100. However, when n2=0, at least one of the X moieties is R², and when n5=0, at least one of the X moieties is H.))

A glycerin derivative having one reactive unsaturated group per molecule, which is used in the synthesis of the glycerin derivative-modified silicone, is preferably (a) a glycerin derivative having a carbon-carbon double bond at the terminal of molecular chain. These are diglycerin derivatives having reactive functional groups such as alkenyl groups at the terminals of the molecular chains of allyl diglycerol, allyl diglycidyl ether, diglycerin monoallyl ether, or the like and can be synthesized by a publicly known method.

In the diglycerin derivative-modified silicone of the present invention, component (a) is specifically a diglycerin monoallyl ether or diglyceryl eugenol from the perspective of use as an emulsifier for a water-in-oil emulsion, in particular, use as an emulsifier for a water-in-oil emulsion, use as a surfactant or a dispersant, or use in a cosmetic composition capable of providing a stable composition in which an oil agent is a continuous phase (water-in-oil emulsion composition or powder-in-oil dispersion).

The (c) long chain hydrocarbon compound having one reactive unsaturated group in each molecule is preferably a monounsaturated hydrocarbon having from 9 to 30 carbon atoms and is more preferably a 1-alkene. Examples of the 1-alkene include 1-nonene, 1-decene, 1-undecene, 1-dodecene, 1-tridecene, 1-tetradecene, 1-hexadecene, and 1-octadecene, and an alkene providing an alkyl group or an aralkyl group listed as an example of R² can be selected as a raw material as desired.

The (d) siloxane dendron compound that has one reactive unsaturated group per molecule and is used in the synthesis of the diglycerin derivative-modified silicone of the present invention is preferably a compound having a siloxane dendron structure with one carbon-carbon double bond at a molecular terminal, and is represented by the following general formula (3'):

[Formula 30]

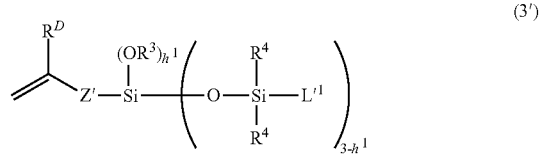

(3')

{wherein
R³ and R⁴ are synonymous with those described above, $R^D$ is a hydrogen atom or a methyl group;
Z' is a divalent organic group;
$h^1$ is a number in a range of 0 to 3;
$L'^1$ is R⁴ moiety or, when j=1, a silylalkyl group represented by the following general formula (3"):

[Formula 31]

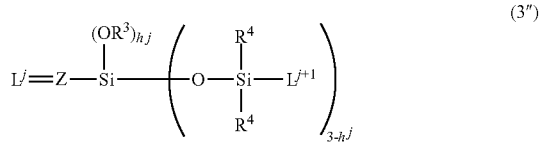

(3")

(wherein R³ and R⁴ are synonymous with those described above;
Z is a divalent organic group;
j represents the generation of the silylalkyl group that is represented by $L^j$, when the number of generations serving as a number of repetitions of the silylalkyl group is k', j is an integer of 1 to k', and the number of generations k' is an integer of 1 to 9; $L^{j+1}$ is the silylalkyl group when j is less than k' and is the R⁴ moiety when j=k'; and
$h^j$ is a number in a range of 0 to 3}.

The (e) chain organopolysiloxane having one reactive unsaturated group per molecule used in the synthesis of the diglycerin derivative-modified silicone of the present invention is preferably a monounsaturated chain siloxane compound represented by the following general formula (2-1):

[Formula 32]

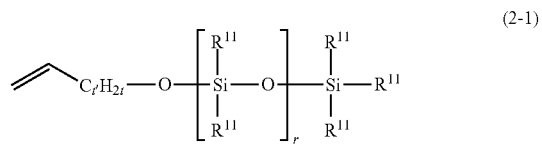

(2-1)

(wherein $R^{11}$ is synonymous with those described above, t' is a number in a range of 0 to 8, and r is a number in a range of 1 to 500). Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

As (f) an unsaturated short-chain hydrocarbon compound (halogen atom-substituted or unsubstituted) having from 2 to 8 carbon atoms having one reactive unsaturated group per molecule that can be used in the synthesis of the diglycerin derivative-modified silicone of the present invention, a monounsaturated hydrocarbon having from 2 to 8 carbon atoms is preferable, and 1-alkene is more preferable. Examples of 1-alkenes include ethylene, propylene, 1-butene, 1-hexene, and 1-octene.

The hydrosilylation reaction used to synthesize the diglycerin derivative-modified silicone or a composition containing the same can be carried out in accordance with a publicly known method in the presence or absence of a solvent. Here, examples of the reaction solvent include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; and chlorinated hydrocarbon-based organic solvents such as carbon tetrachloride.

The hydrosilylation reaction may be performed in the presence or absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. If a platinum catalyst is used, the usage quantity of the catalyst is approximately 0.0001 to 0.1 mass %, and preferably 0.0005 to 0.05 mass %, but is not particularly limited. A reaction temperature of the hydrosilylation reaction is typically from 30 to 120° C., and a reaction time is typically from 10 minutes to 24 hours and preferably from 1 to 10 hours.

When the hydrosilylation reaction is performed, the ratio of the [substance amount of carbon-carbon double bonds in glycerin derivative group-containing compound/substance amount of silicon-bonded hydrogen atoms to be added to the carbon-carbon double bonds of the glycerin derivative group-containing compound in the organohydrogenpolysiloxane] is preferably in a range of 0.8 to 1.5, and more preferably in a range of 1.0 to 1.3. That is, when synthesizing the diglycerin derivative-modified silicone of the present invention, it is preferable to use a slight excess of a diglycerin derivative group-containing compound. Although processing with the ratio above 1.5 is also possible, the proportion of residual starting material increases, so it is not economical. Furthermore, when the ratio is in a range of 0.8 to 1.0, the amount of the silicon-bonded hydrogen atoms consumed by the hydrosilylation reaction falls into the range from 0.8 to 1.0, and silicon-bonded hydrogen atoms remain at the ratio of 0 to 0.2. However, it is possible to cause dehydrogenation reactions with hydroxyl groups contained in the glycerin derivative group and alcoholic hydroxyl groups of the reaction solvent, which can consume the remaining silicon-bonded hydrogen atoms, depending on the reaction conditions.

On the other hand, if the ratio is less than 0.8, there is a risk that unreacted organohydrogenpolysiloxane will remain. When such a diglycerin derivative-modified silicone is used as the raw material for an external use preparation or a cosmetic composition, the remaining organohydrogenpolysiloxane might react with the other raw materials, and generate hydrogen gas. This might cause such undesirable effects as alteration of the external use preparation or the cosmetic composition at the incorporation destination, fire, container expansion, and the like. In addition, when an attempt is made to consume the remaining silicon-bonded hydrogen atoms by using a dehydrogenation reaction when the ratio is less than 0.8, the proportion of Si—O—C crosslinked bonds increases, which increases the tendency to cause gelation during production. Therefore, to enable the complete and safe consumption of organohydrogenpolysiloxane, it is preferable that the ratio exceeds 0.8, i.e., that 0.8 equivalent weight or more of the glycerin derivative group-containing compound is reacted.

In addition, in the synthesis of the diglycerin derivative-modified silicone of the present application, a method common to the reaction, purification, and odor reduction treatment with an acidic substance disclosed by the present applicant in paragraphs [0110] to [0122] of Patent Document 8 (WO/2011/049248) may be used. In particular, since the primary application of the diglycerin derivative-modified silicone of the present invention is a cosmetic composition or an external use preparation, it is particularly preferable to perform purification and odor reduction treatment with an acidic substance from the perspective of safety and odor.

From the perspective of odor reduction, the diglycerin derivative-modified silicone of the present invention is preferably treated with at least one type of an acidic inorganic salt (preferably sodium bisulfate or the like) characterized in that the acidic inorganic salt is a solid at 25° C. and is water soluble, and that the pH at 25° C. of an aqueous solution prepared by dissolving 50 g of the acidic inorganic salt in 1 L of ion exchanged water is at most 4. For example, this refers to (1) decomposition treatment performed by adding the acidic inorganic salt to a reaction system of a diglycerin derivative-modified polysiloxane composition synthesized by a hydrosilylation reaction (e.g. in a flask or other reaction vessel), and then stirring; (2) hydrolysis treatment performed by adding an acidic inorganic salt and water, or an acidic inorganic salt, water, and a hydrophilic solvent and then stirring; and the like. The treatment process that uses the acidic inorganic salt is preferably carried out in the presence of at least one of water and a hydrophilic solvent.

After the odor reduction treatment described above, it is preferable to include a stripping step for removing low-boiling components (propionaldehyde or the like) serving as odor-causing substances, and the treatment with the acidic substance and the stripping of odor-causing substances are preferably performed multiple times.

In addition, after the acid treatment step, it is preferable from the perspective of odor reduction to add an alkaline buffer (trisodium phosphate, tripotassium phosphate, trisodium citrate, sodium acetate, or the like) in an amount corresponding to 100 ppm to 50,000 ppm to the obtained diglycerin derivative-modified silicone or a composition containing the same.

{Composition Containing Diglycerin Derivative-Modified Silicone}

The present invention also relates to a composition containing the diglycerin derivative-modified silicone described above. The composition of the present invention may contain one type of the (A) diglycerin derivative-modified silicone alone or may contain two or more types of the diglycerin derivative-modified silicone.

For example, the (A) diglycerin derivative-modified silicone may be a mixture comprising:

(A1) a high-molecular-weight diglycerin derivative-modified silicone with a number average molecular weight of at least 20,000 comprising: a halogen atom-substituted or unsubstituted monovalent hydrocarbon group having from 9 to 30 carbon atoms in a molecule; and as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %; and (A2) a low-molecular-weight diglycerin derivative-modified silicone with a number average molecular weight of less than 20,000 comprising: a halogen atom-substituted or unsubstituted monovalent hydrocarbon group having from 9 to 30 carbon atoms in a molecule; and as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %. Using such a high-molecular-weight diglycerin derivative-modified silicone and a low-molecular-weight diglycerin derivative-modified silicone in combination makes it possible to improve the emulsifiability with respect to various oil agents and makes it possible to easily control the viscosity of a composition containing the diglycerin derivative-modified silicone.

The compounding ratio of components (A1):(A2) is discretionary, and the components may be used, for example, in combination at a weight (mass) ratio of 1:99 to 99:1, preferably from 10:90 to 90:10, more preferably from 20:80 to 80:20, and even more preferably from 30:70 to 70:30.

The amount occupied by the diglycerin derivative-modified silicone in the composition of the present invention is discretionary. For example, based on the total weight (mass) of the composition, the amount can be set to 0.1 to 99.9 wt. % (mass %) and is preferably from 1 to 99 wt. % (mass %), more preferably from 5 to 80 wt. % (mass %), and even more preferably from 10 to 70 wt. % (mass %). The composition of the present invention may contain water and/or various components described below as raw materials for external use preparations and cosmetic compositions—in particular, oil agents, film-forming agents, powders or powdered coloring agents, ultraviolet light blocking components, polyols, and the like.

{Applications of Diglycerin Derivative-Modified Silicone and Composition Containing the Same}

Next, applications of the diglycerin derivative-modified silicone of the present invention and a composition containing the same will be described in detail.

(Surfactants, Dispersants, Thickening Agents, and Gelling Agents)

Since the diglycerin derivative-modified silicone of the present invention itself has outstanding emulsification performance, it can minutely and stably emulsify and disperse an aqueous phase, a powder, or the like, not only in cases in which the oil phase is a silicone oil or a mixture of a silicone oil, an ester oil agent, or the like, but also when the oil phase primarily consists of a non-polar organic oil such as a mineral oil or isohexadecane, which have been difficult with conventional glycerin-modified silicones. As a result, it is possible to provide a composition having excellent stability over time or with respect to heat. In particular, the diglycerin derivative-modified silicone of the present invention contains a long-chain alkyl group, and it may contain a hydrophobic silylalkyl group having a siloxane dendron structure exhibiting high repellency and/or a chain polysiloxane group as necessary and may have a hydrophilic group together with these components in the same molecule. It is therefore possible to provide stable compositions having a continuous phase as an oil agent (a water-in-oil emulsion composition, a polyol-in-oil emulsion composition, a polar solvent-in-oil emulsion composition, or a powder-in-oil dispersion) to a wide range of oil agent systems, which makes the substance very useful as a surfactant (or emulsifier) or a dispersant. In particular, it is suitable as an emulsifier for a water-in-oil emulsion.

In addition, the diglycerin derivative-modified silicone of the present invention is also useful as a thickening agent (or a gelling agent) in water-in-oil emulsion (also called "W/O emulsion" hereafter) formulations containing various oil agents since it is able to thicken and stabilize emulsification systems containing a wide range of oil agents without necessarily relying on the assistance of an oil thickening agent such as a clay mineral which is hydrophobized and oil-expanded with an organic emulsifier, a quaternary ammonium salt-based organic cation, or the like. A synergistic effect of the oil agent and the diglycerin derivative-modified silicone with regard to the tactile sensation is expressed maximally, and as a result, it is possible to provide an external use preparation or a cosmetic composition in the form of a water-in-oil emulsion which is soft and natural, is smooth and light with good spread, and has an excellent moisturizing feel.

In addition, the use of the novel diglycerin derivative-modified silicone of the present invention and/or a composition containing the same as a surfactant is common to the use of a co-modified organopolysiloxane as a surfactant and the preparation of various emulsification compositions disclosed by the present applicant in paragraphs [0124] to [0147] of Patent Document 8 (WO/2011/049248). In particular, the diglycerin derivative-modified silicone of the present invention is suitable as a surfactant used in a water-in-oil emulsion cosmetic composition.

Since the diglycerin derivative-modified silicone of the present invention can function as both an emulsifier and a thickening agent, it can be used as a thickening emulsifier capable of providing stable compositions having a continuous phase as an oil agent (water-in-oil emulsion composition, polyol-in-oil emulsion composition, polar solvent-in-oil emulsion composition, or powder-in-oil dispersion). In particular, an emulsifier for a water-in-oil emulsion can be suitably used as a thickening emulsifier for not only water-in-oil emulsions in which an aqueous phase is dispersed in an ordinary oil phase, but also polyol-in-oil emulsions in which a polyol phase is dispersed in an oil phase or polar solvent-in-oil emulsions in which a polar solvent is dispersed in a non-polar oil phase. Further, of the diglycerin derivative-modified silicones of the present invention, a low-molecular-weight diglycerin derivative-modified silicone having a number average molecular weight of less than 20,000, in particular, has excellent emulsification performance as well as excellent performance as a dispersant for uniformly dispersing various powders in an oil phase and as a surface treatment agent of various powders. Therefore, it can be used as a powder dispersant or a treatment agent as desired at the time of the preparation of a water-in-oil emulsion.

(Other Applications)

The diglycerin derivative-modified silicone of the present invention or a composition containing the same can be applied to applications common to the co-modified organopolysiloxane described in Patent Document 8 (WO/2011/049248) and can be used. The diglycerin derivative-modified silicone may be compounded with various cosmetic compositions in the same manner as the co-modified organopolysiloxane disclosed in Patent Document 8 in applications as a surfactant (emulsifier) or various treatment agents (powder dispersant or surface treatment agent), particularly applications as an emulsifier or powder treatment agent and applications as a cosmetic raw material, combinations with discretionary cosmetic raw material components, and the dosage forms, types, and formulation examples of external use preparations and cosmetic compositions, in particular. The diglycerin derivative-modified silicone of the present invention and a composition containing the same have an excellent tactile sensation and have an outstanding capacity to stably emulsify and disperse an aqueous phase alone and a capacity to stably disperse a powder in a wide range of oil agents. The diglycerin derivative-modified silicone has advantages in that it can provide, in each of the applications of the co-modified organopolysiloxane disclosed in Patent Document 8, an external use preparation or a cosmetic composition in which the degree of freedom of the formulation of the external use preparation or cosmetic composition is further broadened, the effect of the cosmetic is improved, the tactile sensation and stability over time is further improved on the whole, and the external use preparation or cosmetic composition is improved to a PEG-free formulation as necessary. In addition, of the diglycerin derivative-modified silicones of the present invention, a high-molecular-weight diglycerin derivative-modified silicone having a number average molecular weight of at least 20,000, in particular, can also be applied to applications common to the co-modified organopolysiloxane described in Patent Document 9 (WO/2011/049247) and can be used. The diglycerin derivative-modified silicone of the present invention may be compounded with various cosmetic compositions in the same manner as the co-modified organopolysiloxane disclosed in Patent Document 9 with regard to applications as a thickening agent of an oily raw material and applications as a raw material for an external use preparation or cosmetic composition, combinations with discretionary cosmetic raw material components, and gel-like compositions containing the co-modified organopolysiloxane and a cosmetic composition or the like using the same.

The diglycerin derivative-modified silicone of the present invention or a composition containing the same is a material which is particularly superior as a surfactant, an emulsifier, a (powder) dispersant, or a thickening agent, but it is also effective as a tactile sensation improver, a moisturizing agent, a binder, a surface treatment agent, and a skin adhesive. Additionally, the diglycerin derivative-modified silicone of the present invention, or the composition comprising the same can be combined with water in order to function as a film agent or a viscosity adjusting agent.

Unlike conventional polyether-modified silicone, the diglycerin derivative-modified silicone of the present invention is hardly susceptible to deterioration due to oxidation by oxygen in the air. Therefore, there is no need for the operation of increasing oxidative stability by blending antioxidants such as phenols, hydroquinones, benzoquinones, aromatic amines, or vitamins in order to prevent oxidative degradation. However, stability improves further when such antioxidants, for example, BHT (2,6-di-t-butyl-p-cresol), vitamin E, and the like are added. In this case, the added amount of the antioxidant that is used is in a range (by weight (mass)) from 10 to 1,000 ppm, and preferably from 50 to 500 ppm, of the diglycerin derivative-modified silicone.

(Raw Material for Use in an External Use Preparation or a Cosmetic Composition)

The diglycerin derivative-modified silicone of the present invention can be suitably used as a raw material for an external use preparation and a cosmetic composition used on the human body.

The ratio occupied by the (A) diglycerin derivative-modified silicone of the present invention in the raw material for an external use preparation and a cosmetic composition is preferably from 10 to 100 wt. % (mass %), more preferably from 20 to 100 wt. % (mass %), and even more preferably from 30 to 100 wt. % (mass %) relative to the total weight (mass) of the raw material. This is because the (A) diglycerin derivative-modified silicone of the present invention can be treated as a raw material for an external use preparation or cosmetic composition by diluting the diglycerin derivative-modified silicone with a suitable solvent such as a silicone oil, an organic oil, or an alcohol. A proportion of the raw material compounded in the external use preparation or the cosmetic composition is not particularly limited but, for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) based on the total weight (mass) of the external use preparation or the cosmetic composition.

(External Use Preparation and Cosmetic Composition)

The (A) diglycerin derivative-modified silicone of the present invention and/or a composition containing the same can be suitably blended into an external use preparation or a cosmetic composition and can form the external use preparation or cosmetic composition of the present invention. In particular, since the (A) diglycerin derivative-modified silicone of the present invention itself has outstanding emulsification performance, it can minutely and stably emulsify and disperse an aqueous phase, a powder, or the like, not only in cases in which the oil phase is a silicone oil, an ester oil, or a triglyceride, but also when the oil phase primarily consists of a non-polar organic oil such as a mineral oil or isododecane, which have been difficult with conventional glycerin-modified silicones. As a result, it is possible to provide a composition having excellent stability over time or with respect to heat, so the substance can be suitably blended into an external use preparation or cosmetic composition in the form of a water-in-oil emulsion or a polyol-in-oil emulsion.

In addition, the (A) diglycerin derivative-modified silicone of the present invention is advantageous in that, it alone has outstanding emulsification performance in comparison to a conventional glycerin-modified silicone. Therefore, it is possible to design a stable cosmetic dosage form and formulation without adding a compound having an oxyalkylene structure with an average value of the number of repetitions of oxyalkylene units of two or more—specifically, a nonionic surfactant having a polyoxyethylene structure. Further, since the diglycerin derivative-containing group does not have a polyoxyethylene (PEG) structure, it does not have the problem of oxidative degradation. In addition, in contrast to a nonionic surfactant having a polyoxyalkylene structure (for example, a polyether-modified silicone), it is possible to suppress the oily feel or stickiness of an external use preparation or cosmetic composition in the form of a water-in-oil emulsion. This makes it possible to provide a W/O emulsion-type external use preparation or cosmetic composition which is soft and natural, is smooth and light with good spread, and has an excellent moisturizing feel.

Therefore, in an external use preparation or cosmetic composition containing the (A) diglycerin derivative-modified silicone of the present invention, when selecting a composition of an end consumer product such as a cosmetic with a PEG-FREE formulation on the whole so as to essentially overcome problems associated with the oxidative degradation of polyoxyethylene (PEG) and to have an excellent tactile sensation, it is very preferable not to add a compound having an oxyalkylene structure having an average value of the number of repetitions of oxyalkylene units of two or more. This object which the (A) diglycerin derivative-modified silicone of the present invention can achieve is difficult to be achieved with a conventional glycerin-modified silicone.

The external use preparation is a product to be applied to human skin, nails, hair, and the like and, for example, medicament active components can be compounded therein and used in the treatment of various disorders. The cosmetic composition is also a product to be applied to human skin, nails, hair, and the like, and is used for beauty purposes. The external use preparation or cosmetic composition is not limited, but is preferably an antiperspirant, a skin cleansing agent, a skin external use preparation, a skin cosmetic composition, a make-up material, an oil-based cosmetic composition, a skin care cosmetic composition, a hair cleansing agent, an external use preparation for hair, or a hair cosmetic composition.

The antiperspirant, skin cleansing agent, skin external use preparation, or skin cosmetic composition of the present invention contains an emulsifier for a water-in-oil emulsion or a powder dispersant containing the diglycerin derivative-modified silicone of the present invention. The form thereof is not particularly limited, but it may be in the form of a solution, milk-like, cream-like, solid, semi-solid, paste-like, gel-like, powder-like, multi-layer, mousse-like, or a water-in-oil or oil-in-water emulsion composition. Specific examples of the skin external use preparation or the skin cosmetic composition product of the present invention include toilet water, emulsions, creams, sunscreen emulsions, sunscreen creams, hand creams, cleansing compositions, massage lotions, cleansing agents, antiperspirants, deodorants, and similar basic cosmetic products; foundations, make-up bases, blushers, rouges, eye shadows, eye liners, mascaras, nail enamels, and similar make-up cosmetic products; and the like.

Similarly, the hair cleansing agent, hair external use preparation or the hair cosmetic composition product of the present invention contains the diglycerin derivative-modified silicone of the present invention and can be used in various forms. For example, the hair cleansing agent, the hair external use preparation or the hair cosmetic composition product of the present invention may be dissolved or dispersed in an alcohol, a hydrocarbon, a volatile cyclic silicone, or the like and used. Furthermore, these may be used in the form of an emulsion by dispersing these in water using an emulsifier. Additionally, the hair cleansing agent, the hair external use preparation or the hair cosmetic composition product of the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. These various forms can be used as shampooing agents, rinsing agents, conditioning agents, setting lotions, hair sprays, permanent wave agents, mousses, hair colorants, and the like.

In addition, the type, form and container of the cosmetic composition or external use preparation composition of the present invention are the same as those disclosed by the present applicant in paragraphs [0230] to [0233] and the like of Patent Document 8 (WO/2011/049248).

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

[(B) Water]It is possible to further blend (B) water into the cosmetic composition or external use preparation of the present invention, and the cosmetic composition or external use preparation of the present invention may be in the form of a water-in-oil type emulsion. In this case, the cosmetic composition or the external use preparation of the present invention exhibits superior emulsion stability and sensation during use. The preparation of a hydrous cosmetic composition or emulsion cosmetic composition is the same as that disclosed by the present applicant in paragraphs [0128] to [0147] in the above-mentioned Patent Document 8 (WO/2011/049248).

(C) Oil Agent

The oil agent used in the cosmetic composition or external use preparation of the present invention is preferably (C) one or more types of oil agents selected from volatile silicone oils, volatile non-silicone oils (organic oils), nonvolatile silicone oils, and nonvolatile silicone oils that are in the form of liquid at 5 to 100° C. Preferable non-silicone oils are hydrocarbon oils, fatty acid ester oils, and liquid fatty acid triglycerides. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents. Emulsifiers and powder dispersants containing the diglycerin derivative-modified silicone exhibit excellent compatibility and dispersibility with respect to these non-silicone oil agents. Therefore, hydrocarbon oil and fatty acid ester oil can be stably blended into a cosmetic composition, and the moisture retaining property of these non-silicone oil agents can be retained. Accordingly, emulsifiers and powder dispersants containing the diglycerin derivative-modified silicone can improve the compounding stability in cosmetic compositions of these non-silicone oil agents.

In addition, by using a non-silicone oil such as a hydrocarbon oil or a fatty acid ester oil in combination with a silicone oil, in addition to the refreshing tactile sensation unique to silicone oils, moisture is retained on the skin, and a moisturizing feel on the skin or hair (also referred to as a "moist feel") or a smooth tactile sensation can be imparted to the cosmetic composition. Moreover, there is an advantage in that the stability over time of the cosmetic composition will not be lost. Furthermore, with a cosmetic composition containing a non-silicone oil and a silicone oil, these moisturizing components (non-silicone oils such as a hydrocarbon oil and a fatty acid ester oil) can be applied to the skin or hair in a more stable and uniform manner, so the moisturizing effects of the moisturizing components on the skin are improved. Thus, in comparison to a cosmetic composition containing only a non-silicone oil (e.g. a hydrocarbon oil, a fatty acid ester oil, or the like), a cosmetic composition containing a silicone oil along with a non-silicone oil is advantageous in that a smoother, more luxurious tactile sensation can be imparted.

These oil agents are the same as those disclosed by the present applicant in paragraphs [0130] to [0135], paragraph [0206], and the like of Patent Document 8 (WO/2011/049248). Examples of the fluorine-based oil include perfluoropolyether, perfluorodecalin, perfluorooctane, and the like.

[(D) Film-Forming Agent]Any type of film-forming agent may be used in the cosmetic composition or external use preparation of the present invention (however, excluding substances falling under the category of component (A)), but it is preferable to use at least one type selected from the group consisting of silicone resins, acryl silicone dendrimer copolymers, polyamide-modified silicones, alkyl-modified silicone waxes, alkyl-modified silicone resin waxes, norbornane-modified silicones, silicone-modified pullulan, organic film forming polymers, and non-aqueous or aqueous dispersions of film-forming polymers. The silicone resins, acryl silicone dentrimer copolymers, polyamide-modified silicones, alkyl-modified silicone waxes, and alkyl-modified silicone resin waxes are the same as those disclosed by the present applicant in paragraphs [0170] to [0173], paragraphs [0177] to [0194], and the like in Patent Document 8 (WO/2011/049248).

Fat-soluble and fat-dispersible film-forming polymers and mixtures thereof can be used as film-forming polymers, and preferable examples of fat-soluble film-forming polymers include olefins, cyclic olefins, butadienes, isoprenes, styrenes, vinyl ethers, esters or amides, or fat-soluble amorphous homopolymers and copolymers of straight-chain, branched, or cyclic (meth)acrylic acid esters or amides containing $C^4$ to $C_{50}$ alkyl groups; amorphous fat-soluble polycondensates; amorphous fat-soluble polysaccharides containing an alkyl sidechain (ether or ester); vinyl pyrrolidone (VP) copolymers; acrylic silicone graft polymers containing an acrylic skeleton and a silicone graft or containing a silicone skeleton and an acrylic graft; and mixtures thereof. In addition, the film-forming polymer may be at least one diblock or triblock coplymer. A triblock copolymer is preferably a polystyrene/polyisoprene, polystyrene/polybutadiene, polystyrene/copoly(ethylene-butylene), or polystyrene/copoly(ethylene-propylene) type copolymer. In addition, the film-forming polymer may be polyisobutylene, a dextrin isostearic acid (emery type) ester, a rosin acid resin, a candelilla resin, a substituted silylalkyl carbamate polyvinyl alcohol, an esterified product of glycerin and rosin, pentaerythrite rosinate, hydrogenated glyceryl abietate, a polyvinyl isobutyl ether, nitrocellulose, an acylated polysaccharide, glyceryl (behenate/eicosanoic diacid), a silicone-modified olefin wax, a silicone-modified hyaluronic acid, a terpene resin, a fructooligosaccharide fatty acid ester, an α-olefin oligomer, a hydrocarbon resin, a shellac, a polyethylene wax, an inulin fatty acid ester, a solid dialkylketone, silicone-modified cellulose, an alkyd resin, a long-chain alkoxy-modified silicone, an amorphous poly (cycloolef in), or a polyester oligomer.

In addition, a fat-dispersible film-forming polymer is preferably selected from polyurethane, polyurethane-acryl, polyurea, polyurea-polyurethane, polyester-polyurethane, polyether-polyurethane, polyesters, polyester amides, aliphatic polyesters, alkyds, acrylic and/or vinyl polymers or copolymers, acrylic-silicone copolymers, polyacrylamide, polyurethane-silicone polymers, polyurethane acrylate-silicone polymers, polyether polyurethane-silicone polymers, fluoropolymers, and mixtures thereof. Fat-dispersible polymers and mixtures thereof preferably have a glass transition temperature (Tg) of at most 40° C. (more preferably in a range of −10° C. to 30° C.). In addition, the polymer preferably contains at least a soft (low-Tg) block and a hard (high-Tg) block in the molecular structure thereof. The film-forming polymer is preferably present at a solid content in a range of 0.1 to 25 wt. % (mass %) (preferably from 1 to 20 wt. % (mass %), and more preferably from 5 to 16 wt. % (mass %)) with respect to the total weight (mass) of the composition.

As a non-aqueous dispersion liquid of a film-forming polymer, a substance in which microparticles of the aforementioned film-forming polymer are dispersed in a silicone-based oil medium, an organic oil medium, or a mixed oil medium thereof may be preferably used. In addition, these film-forming polymer particles may assume a core/shell structure. For example, a structure in which the inside surfaces of acrylic copolymer particles are coated with an olefin copolymer and stabilized may be used, or a form in which the core/shell particles thereof are dispersed in an oil medium may be used. Alternatively, a structure in which the inside surfaces of olefin copolymer particles are coated with an acrylic (co)polymer and stabilized may conversely be used, or a form in which the core/shell particles thereof are dispersed in an oil medium may be used.

The aqueous dispersion liquid of a film-forming polymer may be an aqueous dispersion of insoluble particles of the polymer, examples of which include aqueous dispersions obtained by the polymerization or copolymerization of monomers selected from styrene, butadiene, ethylene, propylene, vinyl toluene, vinyl propionate, vinyl alcohol, acrilonitrile, chloroprene, vinyl acetate, urethane, isoprene, isobutene, vinyl ether, vinyl pyrrolidone, vinyl imidazole, acrylic acids or methacrylic acids, maleic acid, crotonic acid, or itaconic acid, and esters or amides thereof. Aqueous dispersion liquids of hydroxyethyl methacrylate/methyl methacrylate/methacrylic acid/butyl acrylate copolymers, ethyl acrylate/methacrylic acid/t-butyl acrylate copolymers, and methyl methacrylate/acrylic acid/butyl acrylate copolymers are preferable. As an aqueous dispersion liquid of a film-forming polymer, a substance in which microparticles of the aforementioned film-forming polymer are dispersed in an aqueous medium (medium containing water) may be preferably used. In addition, these film-forming polymer particles may assume a core/shell structure. For example, a structure in which the inside surfaces of olefin copolymer particles are coated with an acrylic copolymer and stabilized may be used, or a form in which the core/shell particles thereof are dispersed in an aqueous medium may be used. Alternatively, a structure in which the inside surfaces of acrylic copolymer particles are coated with an olefin (co)polymer and stabilized may conversely be used, or a form in which the core/shell particles thereof are dispersed in an aqueous medium may be used.

In addition, the film-forming polymer may be a carboxyvinyl polymer or an alkyl-modified carboxyvinyl polymer, an alkyl acrylate copolymer, an oxazoline-modified silicone, or a water-soluble polymer. Any amphoteric, cationic, anionic, non-ionic, or water-swellable clay mineral may be used as an aqueous polymer as long as it is a substance used in ordinary cosmetic compositions, and one type or two or more types of aqueous polymers may also be used in combination. These aqueous polymers or the like have a thickening effect on hydrous components, the aqueous phase, or the polyol phase and are therefore useful for obtaining a gel-like hydrous cosmetic composition, a water (polyol)-in-oil emulsion cosmetic composition, or an oil-in-water emulsion cosmetic composition.

Examples of natural water-soluble polymers include vegetable-based polymers such as Arabic gum, tragacanth gum, galactan, guar gum, carob gum, karaya gum, carrageenan, pectin, agar, quince seed (*Cydonia oblonga*), algal colloid (phaeophyceae extract), starch (rice, corn, potato, or wheat), and glycyrrhizinic acid; microorganism-based polymers such as xanthan gum, dextran, succinoglucan, pullulan, and gellan gum; and animal-based polymers such as collagen, casein, albumin, and gelatin. Additionally, examples of semisynthetic water-soluble polymers include starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate, and the like. Examples of synthetic water-soluble polymers include vinyl-based polymers such as polyvinylalcohol, polyvinyl methyl ether-based polymers, polyvinylpyrrolidone, carboxyvinyl polymers (CARBOPOL 940, CARBOPOL 941; manufactured by the Lubrizol Corporation); polyoxyethylene-based polymers such as polyethyleneglycol 20,000, polyethyleneglycol 6,000 and polyethyleneglycol 4,000; copolymer-based polymers such as polyoxyethylene-polyoxypropylene copolymers and PEG/PPG methyl ethers; acryl-based polymers such as polysodium acrylate, polyethyl acrylate, and polyacrylamide; polyethylene imines; and cationic polymers. Water-swellable clay minerals are inorganic water-soluble polymers, which are a type of colloid-containing aluminum silicate having a three-layer structure. Specific examples include bentonite, montmorillonite, beidellite, nontronite, saponite, hectorite, aluminum magnesium silicate, and silicic anhydride, and these may be used as either natural products or synthetic products.

Examples of film-forming polymers or water-soluble polymers that can be particularly suitably blended into a hair cosmetic composition are cationic water-soluble polymers. Specific examples of cationic water-soluble polymers include quaternary nitrogen-modified polysaccharides (for example, cation-modified cellulose, cation-modified hydroxyethylcellulose, cation-modified guar gum, cation-modified locust bean gum, cation-modified starch, and the like); dimethyldiallylammonium chloride derivatives (for example, copolymers of dimethyldiallylammonium chloride and acrylamide, dimethylmethylene piperidinium polychloride), and the like); vinylpyrrolidone derivatives (for example, copolymer salts of vinylpyrrolidone and dimethylaminoethyl methacrylic acid, copolymers of vinylpyrrolidone and methacrylamide propyltrimethylammonium chloride, copolymers of vinylpyrrolidone and methylvinylimidazolium chloride, and the like); methacrylic acid derivatives (for example, copolymers of methacryloyl ethyl dimethyl betaine, methacryloyl ethyl trimethyl ammonium chloride, and 2-hydroxyethyl methacrylate, copolymers of methacryloyl ethyl dimethyl betaine, methacryloyl ethyl trimethyl ammonium chloride, and methoxypolyethylene glycol methacrylate, and the like).

In addition, examples of film-forming polymers or water-soluble polymers that can be particularly suitably blended into a hair cosmetic composition are amphoteric water-soluble polymers. Specific examples of amphoteric water-soluble polymers include amphoteric starch, dimethyldiallylammonium chloride derivatives (for example, copolymers of acrylamide, acrylic acid, and dimethyldiallylammonium chloride, and copolymers of acrylic acid and dimethyldiallylammonium chloride), and methacrylic acid derivatives (for example, polymethacryloyl ethyl dimethyl betaine, (methacryloyloxy ethyl carboxy betane/alkyl methacrylate) copolymers, (octyl acrylamide/hydroxypropyl acrylate/butylamino ethyl methacrylate) copolymers, N-methacryloyloxy ethyl, N,N-dimethylammonium-α-methyl carboxybetaine/alkyl methacrylate copolymers, and the like).

[(E) Powder or Coloring Agent] A powder or coloring agent, which is used in the cosmetic composition or external use preparation of the present invention, is one that is commonly used as a component of a cosmetic composition, and includes white or colored pigments and extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 μm. Particularly, when compounding the powder or coloring agent as a pigment, preferably one or two or more selected from an inorganic pigment powder, an organic pigment powder, and a resin powder having an average particle size in a range of 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants disclosed by the present applicant in paragraphs [0150] to [0152] of Patent Document 8 (WO/2011/049248).

Of the powders recited, description of a silicone elastomer powder shall be given. The silicone elastomer powder is a crosslinked product of a straight-chain diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by performing surface treatment using an emulsifier or dispersant containing the diglycerin derivative-modified silicone, it is possible to impart a moist tactile sensation without reducing the suede-like tactile sensation of a silicone elastomer powder. Furthermore, when an emulsifier or a dispersant containing the diglycerin derivative-modified silicone is blended into a cosmetic composition together with a silicone elastomer powder, the dispersion stability of the powder in the overall cosmetic composition is improved, and it is possible to obtain a cosmetic composition that is stable over time.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range of 0.1 to 50 µm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those disclosed by the present applicant in paragraph [0168] of Patent Document 8 (WO/2011/049248), and may be a silicone elastomer powder that has been subjected to a variety of water-repellent treatments, as disclosed in paragraphs [0150] to [0152].

It is possible to further blend (F) other surfactants into the cosmetic composition or external use preparation of the present invention. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed by the present applicant in paragraphs [0162], [0163], [0195] to [0201], and the like in Patent Document 8 (WO/2011/049248). An emulsifier containing the diglycerin derivative-modified silicone used in the present invention has a hydrophilic moiety and a hydrophobic moiety in the molecule, and it therefore functions as a powder dispersant. Thus, in cases where used in combination with a silicone-based nonionic surfactant, the emulsifier functions as an aid to enhance the stability of the nonionic surfactant and may improve overall stability of the formulation. In particular, the diglycerin derivative-modified silicone can be advantageously used in combination with three or more polyglyceryl-modified silicones, glyceryl-modified silicones, sugar-modified silicones, and sugar alcohol-modified silicones. Moreover, a silicone-based nonionic surfactant in which an alkyl branch, a straight-chain silicone branch, a siloxane dendrimer branch, or the like is provided simultaneously with the hydrophilic group as necessary can be advantageously used. Here, although it is also possible to use the diglycerin derivative-modified silicone in combination with a polyoxyalkylene-modified silicone or an organic polyoxyalkylene group-containing surfactant, it is preferable to select a surfactant having a non-polyether structure from the perspective of improving the structure of the cosmetic composition or external use preparation to a PEG-FREE formulation on the whole and increasing environmental adaptability.

Depending on the intended use thereof, the cosmetic composition or external use preparation of the present invention can contain one or two or more alcohols, and preferably (G) polyhydric alcohols (polyols) and/or lower monohydric alcohols. These alcohols are the same as those disclosed by the present applicant in paragraphs [0159] and [0160] and the like in Patent Document 8 (WO/2011/049248). However, from the perspective of improving the structure of the cosmetic composition or external use preparation to a PEG-FREE formulation on the whole and increasing environmental adaptability, it is preferable to select a polyhydric alcohol having a non-polyether structure and/or a lower monohydric alcohol. The cosmetic composition or external use preparation of the present invention may have the form of a polyol-in-oil emulsion, for example.

Depending on the purpose thereof, the cosmetic composition or the external use preparation of the present invention can include one or two or more inorganic salts and/or organic salts as a component (H). These salts are the same as those disclosed by the present applicant in paragraph [0161] and the like in Patent Document 8 (WO/2011/049248).

Depending on the purpose thereof, at least one type selected from the group consisting of components (I) including a crosslinking organopolysiloxane, an organopolysiloxane elastomer spherical powder, and a silicone raw rubber can be used in the cosmetic composition or external use preparation of the present invention. These silicone components are the same as those disclosed by the present applicant in paragraphs [0165] to [0169], [0174] to [0176] and the like in Patent Document 8 (WO/2011/049248).

Depending on the purpose thereof, components (J) including J-1) a silicon polyether elastomer gel disclosed in WO/2007/109240 and WO/2009/006091 in which the compatibility with various organic components is enhanced and stable thickening effects are demonstrated as a result of introducing a polyoxypropylene group, commercially available products such as Dow Corning EL-8050 ID SILICONE ORGANIC ELASTOMER BLEND, Dow Corning EL-8051 IN SILICONE ORGANIC ELASTOMER BLEND, Dow Corning EL-7040 HYDRO ELASTOMER BLEND; and J-2): PITUITOUS SILICONE FLUIDS disclosed in WO/2011/028765 and WO/2011/028770 can be used in the cosmetic composition or external use preparation of the present invention. Furthermore, the liquid and slightly-crosslinkable organopolysiloxane proposed by the present applicant in Japanese Patent Application No. 2010-289722 and the domestic priority claimed therefrom can be used in the present invention.

Depending on the purpose thereof, the cosmetic composition or external use preparation of the present invention can contain one or two or more ultraviolet light blocking component as a component (K). These ultraviolet light blocking components are the same as the organic and inorganic ultraviolet light blocking components disclosed by the present applicant in paragraphs [0202] to [0204] and the like in Patent Document 8 (WO/2011/049248). The ultraviolet light blocking components that can be used particularly preferably include at least one type selected from the group consisting of fine particulate titanium oxide, fine particulate zinc oxide, 2-ethylhexyl paramethoxycinnamate, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris[4-(2-ethylhexyloxy-carbonyl)anilino] 1,3,5-triazine {INCI: octyl triazone} and 2,4-bis{[4-(2-ethyl-hexyloxy)-2-hydroxy] phenyl}-6-(4-methoxyphenyl)-1,3,5-triazine {INCI: bis-ethylhexyloxy-phenol methoxyphenyltriazine (trade name: Tinosorb S(™))}. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with an emulsifier or dispersant containing the diglycerin derivative-modified silicone in the cosmetic composition or the external use preparation of the present invention, it is possible to stably disperse the ultraviolet light blocking component in the cosmetic composition while improving the tactile sensation and storage stability of the overall cosmetic composition. It is therefore possible to impart excellent ultraviolet light blocking properties to the cosmetic composition.

Various components other than the components described above can be used in the cosmetic composition or external use preparation of the present invention, provided that such use does not impair the effects of the present invention. Examples thereof include oil-soluble gelling agents, organo-modified clay minerals, preservatives, (N) bioactive components, skin beautifying components, pH adjusting agents, antioxidants, solvents, chelating agents, moisturizing components, and perfumes. These optional cosmetic product components are the same as those disclosed by the present applicant in paragraphs [0207], [0208], [0220] to [0228], and the like in Patent Document 8 (WO/2011/049248).

Additionally, in cases where the cosmetic composition or the external use preparation of the present invention is an antiperspirant, or depending on the purpose thereof, the cosmetic composition or the external use preparation can contain an anti-perspiration active component and/or a deodorant agent. These antiperspiration components and deodorant components are the same as those disclosed by the present applicant in paragraphs [0209] to [0219] and the like in Patent Document 8 (WO/2011/049248). Similarly, in cases in which the cosmetic composition or the external use preparation of the present invention is an antiperspirant composition, the preparation and method of use of the various antiperspirant compositions are the same as those disclosed by the present applicant in paragraphs [0234] to [0275] and the like in Patent Document 8 (WO/2011/049248).

INDUSTRIAL APPLICABILITY

The diglycerin derivative-modified silicone of the present invention and a composition containing the same can be suitably used as a raw material for an external use preparation or a cosmetic composition. Further, due to its excellent properties, in concert with the global trend of improving the structure of end consumer products such as cosmetic products to PEG-FREE formulations on the whole, it is possible to provide an external use preparation or a cosmetic composition in the form of a water (or polyol)-in-oil emulsion, in particular, having excellent stability, usability, and tactile sensation in spite of not containing a compound having a polyoxyethylene part.

PRACTICAL EXAMPLES

The present invention will be described below using practical examples, but the present invention is not limited thereto. In the following compositional formulae, "Me" represents a methyl ($—CH_3$) group, "M" represents a $Me_3SiO$ group (or an $Me_3Si$ group), "D" represents an $Me_2SiO$ group, "$D^H$" represents an MeHSiO group, and "$M^R$" and "$D^R$" respectively represent units in which a methyl group in "M" or "D" is modified by any substituent. Additionally, in the production examples, "IPA" represents isopropyl alcohol. Further, the number average molecular weight of the modified silicone obtained in each practical example is a theoretical value (design value) determined by identifying the average composition formula and the number average molecular weight of methylhydrogenpolysiloxane serving as a starting raw material by means of nuclear magnetic resonance analysis (nuclear species 29Si and 1H) and calculating the value from the molecular weight and reaction rate of each raw material used in the hydrosilylation reaction of each practical example.

Practical Example 1

Synthesis of Long-Chain Alkyl Group-Containing High-Molecular-Weight Diglycerin Derivative-Modified Silicone No. 1

Step 1:

First, 180 g of a methylhydrogenpolysiloxane represented by the average composition formula $MD_{400}D^H{}_{10}M$, and 6.1 g of a vinyl tris(trimethylsiloxy)silane represented by the average composition formula $CH_2=CH—Si(OSiMe_3)_3$, and 60 g of IPA were placed in a reaction vessel. Next, 0.1 g of an IPA solution of a platinum-1,3-divinyl-1,1,3,3-tetramethyldisiloxane complex (Pt concentration: 0.4 wt. %) was added at 60 to 65° C. while stirring under a nitrogen stream. The reaction liquid was heated to 65 to 80° C., and after a reaction was performed for 1 hour, 1 g of the liquid was sampled and it was confirmed by an alkali decomposition gas generation method that target reaction rate had been achieved.

Step 2:

A mixture of 7.8 g of diglycerin monoallyl ether and 10 g of IPA was added to the reaction liquid, and 0.1 g of the same platinum catalyst solution as that described above was further added. When reacted for 1.5 hours at 75 to 80° C., it was confirmed with the same method that the target reaction rate had been achieved.

Step 3:

First, 2.0 g of decene (α-olefin purity=95%) was added to the reaction liquid, and 0.2 g of the same platinum catalyst solution as that described above was further added. After 4.5 hours, 1 g of the reaction liquid was sampled, and it was confirmed by an alkali decomposition gas generation method that the reaction was complete.

Step 4:

The contents of the reaction vessel were heated to 75 to 100° C. and depressurized so as to remove IPA. Next, 193 g of dimethylpolysiloxane (2 cst) was added as a diluent and mixed by stirring so as to homogenize the entire mixture. As a result, 388 g of a composition containing a long-chain alkyl group-containing high-molecular-weight diglycerin derivative-modified silicone represented by the average composition formula $MD_{400}D^{R*11}{}_{2}D^{R*31}{}_{3}D^{R*22}{}_{5}M$ and dimethylpolysiloxane (2 cst) at a mass ratio of 1:1 was obtained as a light brown, opaque, uniform, viscous liquid.

In the formula, $R^{*11}$=—$C_{10}H_{21}$
$R^{*31}$=—$C_2H_4Si(OSiMe_3)_3$
$R^{*22}$=diglycerin portion represented by the average composition formula —$C_3H_6O$—$(C_3H_6O_2)_2$—H Practical Example 2

Synthesis of Long-Chain Alkyl Group-Containing High-Molecular-Weight Diglycerin Derivative-Modified Silicone No. 2

Step 1:

First, 67.1 of a methylhydrogenpolysiloxane represented by the average composition formula $MD_{147}D^{H}{}_{80}M$ and 11.7 g of hexadecene (α-olefin purity=91.7%) (first time) were placed in a reaction vessel. When 0.17 g of an IPA solution of a platinum-1,3-divinyl-1,1,3,3-tetramethyldisiloxane complex (Pt concentration: 0.4 wt. %) was added at room temperature while stirring under a nitrogen stream, heat was generated, and the temperature rose from 18 to 37° C. Further, when 11.7 g of hexadecene (second time) was added in the same manner, the temperature rose from 37 to 50° C. Thereafter, an operation of adding the same amount of hexadecene and reacting the solution when the temperature of the reaction liquid naturally returned to 30 to 40CC was repeated two more times. The reaction liquid was then heated and held at 60 to 70° C., and 0.5 g of the reaction liquid was sampled 3 hours after the reaction was started. It was confirmed by an alkali decomposition gas generation method that the target reaction rate had been achieved.

Step 2:

First, 24.5 g of a diglycerin monoallyl ether, 0.02 g of natural vitamin E, 150 g of IPA, and 150 g of isohexadecane were added to the reaction liquid, and 0.51 g of the same platinum catalyst solution as that described above was further added. A reaction was performed for 5 hours at 60 to 70° C., and it was confirmed with the same method that the target reaction rate had been achieved.

Step 3:

First, 13.2 g (fifth time) of hexadecene (α-olefin purity=91.7%) was added to the reaction liquid, and 0.17 g of the same platinum catalyst solution as that described above was further added. A reaction was performed for 5 hours at 60 to 70° C., and it was confirmed with the same method that the reaction was complete.

Step 4:

An aqueous solution prepared by dissolving 0.027 g of sodium hydrogen sulfate-hydrate in 2.3 g of purified water was added to the contents of the reaction vessel, and acid treatment was performed at 65 to 70° C. while stirring under a nitrogen stream. After low-boiling components such as water and IPA were distilled off at 70° C. under reduced pressure, the pressure was restored when water droplets in the system had disappeared (first acid treatment). Next, 2.3 g of water was added, and after treatment was performed in the same manner, water and other low-boiling components were distilled off. The pressure was then restored when water droplets in the system had disappeared (second acid treatment). The same operation was repeated again (third acid treatment). As a result, 295 g of a composition containing a long-chain alkyl group-containing high-molecular-weight diglycerin derivative-modified silicone represented by the average composition formula $MD_{147}D^{R*13}{}_{55}D^{R*22}{}_{25}M$ and isohexadecane at a mass ratio of 1:1 was obtained as a light brown, opaque, uniform, viscous liquid.

In the formula, $R^{*13}$=—$C_{16}H_{33}$
$R^{*22}$=diglycerin portion represented by the average composition formula —$C_3H_6O$—$(C_3H_6O_2)_2$—H Practical Example 3

Synthesis of Long-Chain Alkyl Group-Containing Low-Molecular-Weight Diglycerin Derivative-Modified Silicone No. 3

Step 1:

First, 3989 g of a methylhydrogenpolysiloxane represented by the average composition formula $MD_{28.7}D^{H}{}_{7.3}M$ and 495 g of a vinyl tris(trimethylsiloxy)silane represented by the average composition formula $CH_2$=$CH$—$Si(OSiMe_3)_3$ were placed in a reaction vessel, and when 7.5 g of an IPA solution of a platinum-1,3-divinyl-1,1,3,3-tetramethyldisiloxane complex (Pt concentration: 0.4 wt. %) was added at 40° C. while stirring under a nitrogen stream, the temperature rose to 70° C. due to heat generation. The reaction liquid was maintained at 55° C., and after a reaction was performed for 3 hours, 0.5 g of the reaction liquid was sampled. It was confirmed with an alkali decomposition gas generation method that there were no problems with the reaction rate.

Step 2:

When 469 g (first time) of hexadecene (α-olefin purity=91.7%) was added to the reaction liquid, heat was generated, and the temperature rose from 50° C. to 68° C. When heat generation subsided, 469 g of hexadecene (second time) was added. Heat was generated again, and the temperature rose from 48° C. to 65° C. After 2 hours, 1 g of the reaction liquid was sampled, and it was confirmed with the same method that the target reaction rate had been achieved.

Step 3:

First, 439 g of a diglycerin monoallyl ether, 0.69 g of natural vitamin E, and 1020 g of IPA were added to the reaction liquid, and 7.5 g of the same platinum catalyst solution as that described above was further added. When reacted for 3 hours at 30 to 65° C., it was confirmed with the same method that the target reaction rate had been achieved.

Step 4:

When 469 g (third time) of hexadecene (α-olefin purity=91.7%) was added to the reaction liquid, the temperature rose from 62 to 68° C. After 1 hour, 469 g of hexadecene (fourth time) was added, and a reaction was performed for 3.5 hours at 60 to 70° C. It was confirmed with the same method that the reaction was complete.

Step 5:

After IPA was removed from the reaction system by depressurization, an aqueous solution prepared by dissolving 1.02 g of sodium hydrogen sulfate-hydrate in 102 g of purified water was added to the contents of the reaction vessel, and acid treatment was performed for 30 minutes at 60 to 70° C. while stirring under a nitrogen stream. Water and low-boiling components were then distilled off under reduced pressure, and the pressure was restored when water droplets in the system had disappeared (first acid treatment). Next, 102 g of water was added, after treatment was performed for 30 minutes in the same manner, water and other low-boiling components were distilled off. The pressure was restored when water droplets in the system had disappeared (second acid treatment). The same operation was repeated again (third acid treatment). Next, after the solution was neutralized by adding 62.1 g of 1 wt. % sodium bicarbonate water, dewatering treatment was again performed under reduced pressure at 60 to 70° C. Finally, the solution was filtered to obtain 6700 g of a composition containing a low-molecular-weight diglycerin derivative-modified silicone containing a long-chain alkyl group represented by the average composition formula $MD_{28.7}D^{R*13}{}_{5.0}D^{R*31}{}_{1}D^{R*22}{}_{1.3}M$ as a light brown, practically transparent, uniform liquid.

In the formula, $R^{*13}=$—$C_{16}H_{33}$ $R^{*31}=$—$C_2H_4Si(OSiMe_3)_3$ $R^{*22}=$diglycerin portion represented by the average composition formula —$C_3H_6O$—$(C_3H_6O_2)_2$—H Practical Example 4

Synthesis of Long-Chain Alkyl Group-Containing Low-Molecular-Weight Diglycerin Derivative-Modified Silicone No. 4

First, 137.7 g of a methylhydrogenpolysiloxane represented by the average composition formula $MD_{42.9}D^H{}_{6.7}M$ and 14.9 g of a 3-methacryloxy propyl(tris(trimethylsiloxy) silylethyl dimethylsiloxy)silane represented by the following average composition formula:

[Formula 33]

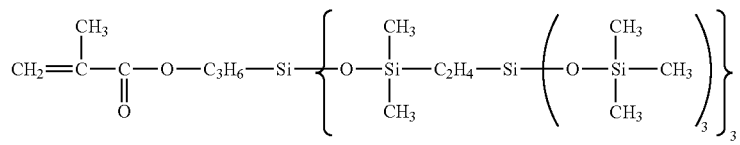

were added to the reaction vessel and heated to 80° C. while stirring under a nitrogen stream. Next, 0.12 mL of an IPA solution of a platinum-1,3-divinyl-1,1,3,3-tetramethyldisiloxane complex (Pt concentration: 0.45 wt. %) was added, and a reaction was performed for 3 hours at 80 to 90° C. A small amount of the reaction liquid was sampled, and it was confirmed with an alkali decomposition gas generation method (the remaining Si—H groups are decomposed using a KOH ethanol/aqueous solution, and the reaction rate is calculated from the volume of the generated hydrogen gas) that the target reaction rate had been achieved. Next, 38.4 g of hexadecene (α-olefin purity: 91.7%) was added to the reaction mixture, and after a reaction was performed for 1 hour at 85 to 105° C., it was confirmed with the same method that the target reaction rate had been achieved. Thereafter, 9.3 g of a diglycerin monoallyl ether and 120 g of IPA were added to the reaction mixture, and 0.20 mL of the platinum catalyst described above was added. After a reaction was performed for 1 hour at 70 to 85° C., the mixture was sampled. As a result of calculating the reaction rate, it was found that a modified silicone intermediate represented by the average composition formula $MD_{42.9}D^{R*32}{}_{0.3}D^{R*22}{}_{0.8}D^{R*134.4}D^H{}_{1.2}M$ had been produced.

Here, $R^{*11}$, $R^{*21}$, and $R^{*32}$ are as follows.

$R^{*13}=$—$C_{16}H_{33}$ $R^{*22}=$diglycerin portion represented by the average composition formula —$C_3H_6O$—$(C_3H_6O_2)_2$—H $R^{*32}=$

[Formula 34]

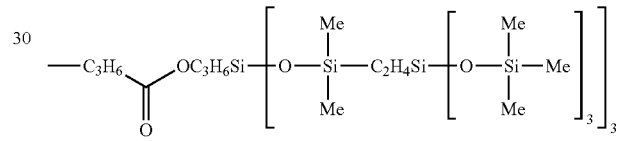

The reaction liquid was cooled to 50° C., and after 2.1 g of 1,5-hexadiene was added thereto, a reaction was performed for 4 hours at 50 to 75° C. In this case, the Vi/H molar ratio upon crosslinking was 1.17. The mixture was sampled, and when the reaction rate was calculated, the reaction substantially has been completed. Thereafter, the low-boiling components were distilled off at 80 to 90° C. under reduced pressure to obtain 190 g of a liquid organo-modified organopolysiloxane having a glycerin derivative group and a crosslinking portion, wherein the crosslinking portion links the organopolysiloxane portion and the organic portion by means of Si—C bonds. This product was a light brown to ash-white colored, uniform, viscous liquid at 25° C.

The average structural formula (schematic diagram) of the liquid organopolysiloxane obtained in Practical Example 4 is illustrated below.

[Formula 35]

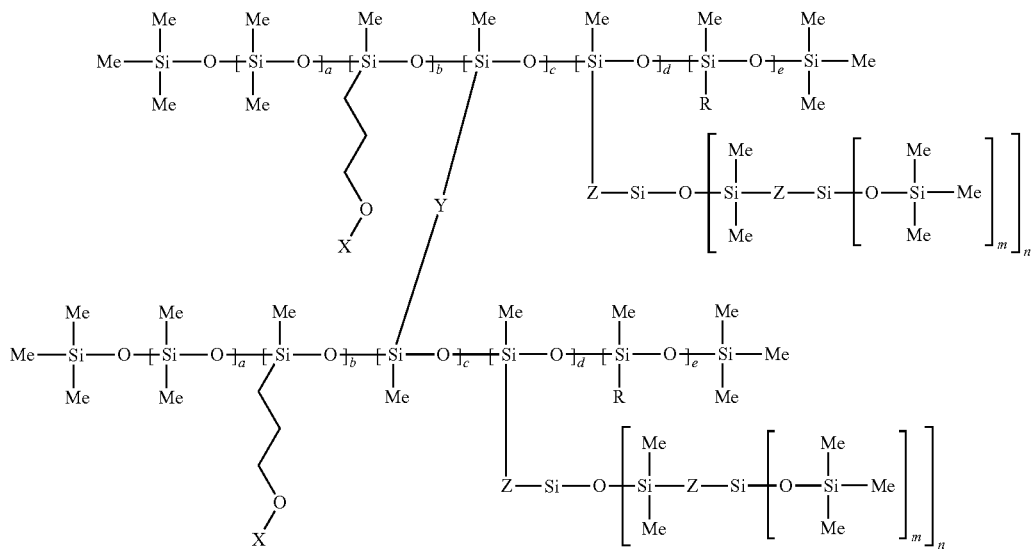

(wherein Me=methyl group; Z in
[ ]n=—CH$_2$CH$_2$—;
Z other than [ ]n=—C$_3$H$_6$—COO—C$_3$H$_6$—; R=—C$_{16}$H$_{33}$;
Y=—(CH$_2$)$_6$—; a=42.9; b=0.8; c=1.2; d=0.3; e=4.4;
m=3; n=3; and X=(C$_3$H$_6$O$_2$)$_2$H.)

Comparative Example 1

Synthesis of Silicone Compound RE-1

First, 212.5 g of a methylhydrogenpolysiloxane represented by the average composition formula MD$_{406}$D$^H_4$M, 4.9 g of a glycerin monoallyl ether represented by the structural formula CH$_2$=CH—CH$_2$—OCH$_2$CH(OH)CH$_2$OH, and 90 g of IPA were added to a reaction vessel, and the mixture was heated to 70° C. while stirring under a nitrogen stream. Next, 0.053 g of an IPA solution of a platinum-1,3-divinyl-1,1,3,3-tetramethyldisiloxane complex (Pt concentration: 4.5 wt. %) was added thereto, and the mixture was reacted for 3 hours at 80° C. Then, 2 g of the reaction liquid was sampled, and it was confirmed with an alkali decomposition gas generation method that the reaction was complete. The reaction liquid was heated under reduced pressure to distill off low-boiling components, and as a result, a high-molecular-weight-monoglycerin-modified silicone not containing a long-chain alkyl group represented by the average composition formula MD$_{406}$DR*$^{21}_4$M was obtained.
In the formula,
R*$^{21}$=—C$_3$H$_6$OCH$_2$CH(OH)CH$_2$OH
This product was a light yellowish-brown, translucent, uniform, viscous liquid.

Comparative Example 2

Synthesis of Silicone Compound RE-2

Step 1:
First, 180 g of a methylhydrogenpolysiloxane represented by the average composition formula MD$_{400}$D$^H_{10}$M, 6.1 g of a vinyl tris(trimethylsiloxy)silane represented by the average composition formula CH$_2$=CH—Si(OSiMe$_3$)$_3$, and 60 g of IPA were placed in a reaction vessel, and 0.15 g of an IPA solution of a platinum-1,3-divinyl-1,1,3,3-tetramethyl-disiloxane complex (Pt concentration: 0.4 wt. %) was added at 60 to 65° C. while stirring under a nitrogen stream. The reaction liquid was heated to 60 to 80° C., and after a reaction was performed for 3 hours, 1 g of the solution was sampled. It was confirmed with an alkali decomposition gas generation method that the target reaction rate had been reached.
Step 2:
A mixture of 10.6 g of a triglycerin monoallyl ether and 10 g of IPA was added to the reaction liquid, and 0.1 g of the same platinum catalyst solution as that described above was further added. When reacted for 1 hour at 75 to 80° C., it was confirmed with the same method that the target reaction rate had been achieved.
Step 3:
First, 1.9 g of decene (α-olefin purity=95%) was added to the reaction liquid, and 0.15 g of the same platinum catalyst solution as that described above was further added. After 3.5 hours, 1 g of the reaction liquid was sampled, and it was confirmed with an alkali decomposition gas generation method that the reaction was complete.
Step 4:
The contents of the reaction vessel were heated to 75 to 105° C. and depressurized so as to remove IPA. Next, 193 g of dimethylpolysiloxane (2 cst) was added as a diluent and mixed by stirring for 4 hours at 70 to 80° C. so as to homogenize the entire mixture. As a result, 390 g of a composition containing a long-chain alkyl group-containing high-molecular-weight triglycerin derivative-modified silicone represented by the average composition formula MD$_{400}$D$^{R*11}_2$D$^{R*31}_3$D$^{R*23}_5$M and dimethylpolysiloxane (2 cst) at a mass ratio of 1:1 was obtained as a light brown, opaque, uniform, viscous liquid.
In the formula,
R*$^{11}$=—C$_{10}$H$_{21}$
R*$^{31}$=—C$_2$H$_4$Si(OSiMe$_3$)$_3$
R*$^{23}$=triglycerin portion represented by the average composition formula —C$_3$H$_6$O—(C$_3$H$_6$O$_2$)$_3$—H

Comparative Example 3

Synthesis of Silicone Compound RE-3

First, 111.6 g of a methylhydrogenpolysiloxane represented by the average composition formula $MD_{61}D^H{}_{15}M$ was placed in a reaction vessel, and a mixture comprising 30.9 g of a single-terminal vinyl-modified dimethylpolysiloxane represented by the structural formula $CH_2=CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise. The mixture was stirred at room temperature so as to obtain a linear siloxane branched polysiloxane intermediate.

In addition, 7.0 g of triglycerin monoallyl ether, 50.4 g of dodecene (α-olefin purity=95.4%), 100 g of IPA, and 0.40 g of an IPA solution of platinum-1,3-divinyl-1,1,3,3-tetramethyldisiloxane complex (Pt concentration: 0.5 wt. %) were added to another reaction vessel, the linear siloxane branched polysiloxane synthesized previously was added dropwise under reflux of a solvent while stirring under a nitrogen stream. After the adding was completed, heating and stirring were continued for 3 hours. Then, 2 g of the reaction liquid was sampled, and it was confirmed with an alkali decomposition gas generation method that the reaction was complete.

Next, the reaction liquid was transferred to an autoclave, and after 4.0 g of a sponge nickel catalyst, 2.0 g of water, and 2.0 g of IPA were added, hydrogen gas was introduced, and hydrogenation treatment was performed over the course of 6 hours under the following conditions: 110° C., 0.9 MPa. Next, the reaction mixture was cooled to 60° C. after the treatment, and after hydrogen gas was blown over the mixture, purging with nitrogen was performed three times. Next, the sponge nickel catalyst was removed via microfiltration. Thus, 204 g of a colorless, transparent filtrate was obtained.

This filtrate was placed in a separate reaction vessel and maintained for 1 hour at 100° C. and 20 Torr under a nitrogen stream so as to distill off low-boiling components. Thus, 138 g of a composition containing a long-chain alkyl group-containing low-molecular-weight triglycerin derivative-modified silicone represented by the $MD_{61}D^{R*12}{}_{12}D^{R*33}{}_{2}D^{R*23}{}_{1}M$ was obtained as a substantially colorless, translucent, uniform liquid.

In the formula,
$R^{*12}$=—$C_{12}H_{25}$
$R^{*33}$=—$C_2H_4SiMe_2(OSiMe_2)_6OSiMe_3$
$R^{*23}$=—$C_3H_6O$—X, where X is the triglycerin portion.

Comparative Example 4

Synthesis of Silicone Compound RE-4

Step 1:

First, 86.6 g of a methylhydrogenpolysiloxane represented by the average composition formula $MD_{360}D^H{}_{18}M$, 4.0 g of a diglycerin monoallyl ether, 0.01 g of natural vitamin E, 100 g of caprylyl methicone (FZ-3196), and 100 g of IPA were added to a reaction vessel, and 0.40 g of an IPA solution of a platinum-1,3-divinyl-1,1,3,3-tetramethyldisiloxane complex (Pt concentration: 0.4 wt. %) was added at room temperature while stirring under a nitrogen stream. A reaction was performed for 5 hours while heating the solution in an oil bath set to 68° C. Two g of the reaction liquid was sampled, and it was confirmed with an alkali decomposition gas generation method that the reaction was complete.

Step 2:

An aqueous solution prepared by dissolving 0.015 g of sodium hydrogen sulfate-hydrate in 1.5 g of purified water was added to the contents of the reaction vessel, and acid treatment was performed for 30 minutes at 70 to 80CC while stirring under a nitrogen stream. After water and low-boiling components were distilled off at 70° C. under reduced pressure, the pressure was restored when water droplets in the system had disappeared (first acid treatment). Next, 1.5 g of water was added, and after treatment was performed for 30 minutes in the same manner, water and other low-boiling components were distilled off, and the pressure was restored when water droplets in the system had disappeared (second acid treatment). The same operation was repeated again (third acid treatment) so as to obtain 196 g of a composition containing a high-molecular-weight diglycerin modified-silicone not containing a long-chain alkyl group represented by the average composition formula $MD_{360}D^{R*22}{}_{18}M$ and caprylyl methicone at a mass ratio of 1:1 as a light brown, opaque, viscous liquid.

In the formula, $R^{*22}$=diglycerin portion represented by the average composition formula —$C_3H_6O$—$(C_3H_6O_2)_2$—H.

The average composition formulae and the like of the "long-chain alkyl group-containing high-molecular-weight diglycerin derivative-modified silicones No. 1 and No. 2" and the "long-chain alkyl group-containing low-molecular-weight diglycerin derivative-modified silicones No. 3 and No. 4" of the present invention as well as the "silicone compound RE-1" to "silicone compound RE-4" of the comparative examples synthesized with the methods described above are shown in Table 1.

TABLE 1

| Compound No. | Average composition formula of modified silicone compound | Long-chain alkyl group (wt. % (mass %)) | Number average molecular weight |
|---|---|---|---|
| No. 1 | $MD_{400}D^{R*11}{}_{2}D^{R*31}{}_{3}D^{R*22}{}_{5}M$ (Diglycerin-modified: Mw > 20,000) | $C_{10}$ (0.87%) | 32,600 |
| No. 2 | $MD_{147}D^{R*13}{}_{55}D^{R*22}{}_{25}M$ (Diglycerin-modified: Mw > 20,000) | $C_{16}$ (37%) | 33,300 |
| No. 3 | $MD_{28.7}D^{R*13}{}_{5.0}D^{R*31}{}_{1}D^{R*22}{}_{1.3}M$ (Diglycerin-modified: Mw < 20,000) | $C_{16}$ (26%) | 4,400 |
| No. 4 | [Formula 35] Reference (Diglycerin-modified: Mw < 20,000) | $C_{16}$ (18%) | 11,000 |
| RE-1 | $MD_{406}D^{R*21}{}_{4}M$ (Monoglycerin-modified: Mw > 20,000) | None | 31,000 |
| RE-2 | $MD_{400}D^{R*11}{}_{2}D^{R*31}{}_{3}D^{R*23}{}_{5}M$ (Triglycerin-modified: Mw > 20,000) | $C_{10}$ (0.87%) | 32,400 |

TABLE 1-continued

| Compound No. | Average composition formula of modified silicone compound | Long-chain alkyl group (wt. % (mass %)) | Number average molecular weight |
|---|---|---|---|
| RE-3 | $MD_{61}D^{R*12}{}_{12}D^{R*33}{}_{2}D^{R*23}{}_{1}M$ (Triglycerin-modified: Mw < 20,000) | $C_{12}$ (24%) | 8,400 |
| RE-4 | $MD_{360}D^{R*22}{}_{18}M$ (Diglycerin-modified: Mw > 20,000) | None | 31,400 |

In Table 1, the classifications and structures of the functional groups are as follows.

<Siloxane Branched Group: R*³>
$R^{*31}$=—$C_2H_4Si(OSiMe_3)_3$
$R^{*33}$=—$C_2H_4SiMe_2(OSiMe_2)_6OSiMe_3$
$R^{*32}$=

[Formula 36]

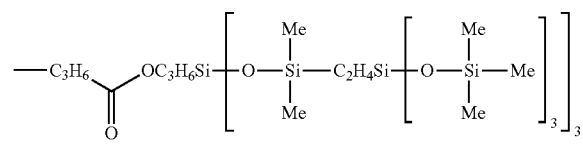

<Hydrophilic Group: R*²>
$R^{*21}$=—$C_3H_6OCH_2CH(OH)CH_2OH$
$R^{*22}$=—$C_3H_6O$—$(C_3H_6O_2)_2$—H
$R^{*23}$=—$C_3H_6O$—$(C_3H_6O_2)_3$—H
<Other Hydrophobic Organic Groups: R*¹>
$R^{*11}$=—$C_{10}H_{21}$
$R^{*12}$=—$C_{12}H_{25}$
$R^{*13}$=—$C_{16}H_{33}$ Practical Examples 5 to 15 and Comparative Examples 5 to 17

Water-in-emulsion compositions having the compositions shown in Tables 2 to 4 were prepared as follows using the silicone compounds obtained in Practical Examples 1 to 4 and Comparative Examples 1 to 4, and the uniformity of the oil phase (compatibility of the oil phase and the emulsifier), the viscosity of the emulsion composition (effect of each silicone compound as a thickening emulsifier), the emulsified particle size, and the stability were evaluated in accordance with the following evaluation criteria. These results are shown collectively in Tables 2 to 4. In the table, "parts" indicates "parts by weight (mass)". In addition, in Tables 3 and 4, Practical Example 7 and Comparative Example 12 are listed in duplicate from the perspective of viewability and comparisons with other practical examples or comparative examples.

[Preparation Method for Water-in-Oil Emulsion Composition]
1. A silicone compound comprising an oil agent and an emulsifier was placed in a 200 mL container.
2. The compound was stirred and the heated as necessary so that the emulsifier was uniformly dispersed or dissolved in the oil agent (oil phase A).
3. Table salt and ion exchanged water were placed in a separate container. The salt was dissolved by mixing using a spatula. Furthermore, 1,3-butylene glycol was mixed and dissolved therein (aqueous phase B).
4. The saw teeth of a homodisper were immersed in the oil phase A, and an aqueous phase B was poured into the oil phase A at a roughly constant rate over a period of approximately 45 seconds at room temperature while stirring at 1000 rpm.
5. The rotational speed of the homodisper was increased to 3500 rpm, and the contents were homogeneously emulsified by stirring for 2 minutes.
6. The homodisper was stopped. The oily component adhering to the inner wall of the container was then scraped off using a spatula and was mixed with the emulsion.
7. The contents were homogeneously emulsified by stirring for 3 minutes with the rotational speed of the homodisper at 3500 rpm.

[Confirmation of Homogeneity of Oil Phase A] The homogeneity of the oil phase A—that is, the compatibility of the emulsifier and the oil agent system—was evaluated in accordance with the following evaluation criteria.
⊚: transparent or nearly transparent, uniform liquid
○: translucent, uniform liquid
Δ: roughly uniform dispersion liquid which is opaque or has a slightly translucent feel, with a slight separating tendency
x: The emulsifier is completely incompatible with the oil agent, and the substance is suspended in a separated/sedimented or scummy state.

[Viscosity Measurement] In order to evaluate the thickening stabilizing effect of an emulsion of the silicone compound serving as an emulsifier, viscosity measurements were taken for each water-in-oil emulsion composition at 25° C. with a type E viscometer.

[Emulsion Particle Size Measurement and Stability Evaluation] The day after each water-in-oil emulsion composition was prepared and after each water-in-oil emulsion composition was left to stand for 1 month at 50° C., the compositions were observed (1000× magnification) and photographed with an optical microscope, and the weight average particle size was computed using image analysis software. As a result, the initial stability of the emulsified particle size and the stability of the emulsified particle size over time were evaluated. When particle coalescence was observed, this was noted in the tables.
⊚: The change in the emulsified particle size is small, and no signs of coalescence are observed.
○: The emulsified particle size may have increased slightly, but no clear coalescence is observed. In addition, even if there is an increase in the emulsified particle size, the overall particle size is small, and the emulsification system is maintained.
Δ: Some particle coalescence is considered to have occurred, and the maximum emulsified particle size has clearly increased.
x: Coalescence occurs in many particles, and emulsification is breaking down (cases in which emulsification itself fails are also denoted as "x").

[Emulsion Thickening or Viscosity Evaluation] Performed freely: The emulsion viscosity can be maintained at a high level with an emulsifier. Alternatively, the emulsion viscosity can be adjusted between a low viscosity and a high viscosity by using two types of emulsifiers of different molecular weights in combination.

Difficult: Only a low-viscosity emulsion is obtained with an emulsifier. It is necessary to use a separate oil thickening agent or a gelling agent in combination in order to obtain a high-viscosity emulsion.

x: A stable emulsion cannot be formed from the start.

TABLE 2

Water-in-oil emulsion composition formulations and evaluation results
(Practical Examples 5 and 6 and Comparative Examples 5 to 11)

| Raw material name & silicone compound No. | Practical Example | | Comparative Example | | | | | | |
|---|---|---|---|---|---|---|---|---|---|
| | 5 | 6 | 5 | 6 | 7 | 8 | 9 | 10 | 11 |
| No. 1 (Concentration: 50 wt. %) | 4 | 4 | — | — | — | — | — | — | — |
| RE-1 (Concentration: 100 wt.%) | — | — | 2 | 2 | — | — | — | — | — |
| RE-2 (Concentration: 50 wt. %) | — | — | — | — | 4 | 4 | — | — | — |
| RE-3 (Concentration: 100 wt. %) | — | — | — | — | — | — | 2 | 2 | — |
| RE-4 (Concentration: 50 wt. %) | — | — | — | — | — | — | — | — | 4 |
| Dimethylpolysiloxane (6 cst) | 21 | 9.5 | 23 | 11.5 | 21 | 9.5 | 23 | 11.5 | 21 |
| Mineral oil 50SUS (37.8° C.) | — | 11.5 | — | 11.5 | — | 11.5 | — | 11.5 | — |
| Sodium chloride | 0.5 | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 | 68.5 |
| 1,3-Butylene glycol | 6 | 6 | 6 | 6 | 6 | 6 | 6 | 6 | 6 |
| Homogeneity of oil phase | ○ | ○ | ◎ | Separated | Separated | Separated | ◎ | ◎ | Separated |
| Emulsion viscosity (25° C.)[Pa·s] | 108 | 99 | 32 | — | — | — | 15 | 12 | — |
| Weight average particle size Day after preparation (μm) | 2 | 3 | 7 Coalescence | — | — | — | 5.9 | 6.0 | — |
| Weight average particle size After one month (50° C.) (μm) | 3 | 3 | 8 Coalescence | — | — | — | 7 | 8 | — |
| Stability of emulsified particles | ◎ | ◎ | X | X | X | X | Δ | Δ | X |
| Emulsion thickening effect | ◎ | ◎ | Δ | X | X | X | X | X | X |

TABLE 3

Water-in-oil emulsion composition formulations and evaluation results
(Practical Examples 7 and 11 and Comparative Examples 12 to 15)

| Raw material name & silicone compound No. | Practical Example | | | | | Comparative Example | | | |
|---|---|---|---|---|---|---|---|---|---|
| | 7 | 8 | 9 | 10 | 11 | 12 | 13 | 14 | 15 |
| No. 2 (Concentration: 50 wt. %) | 4 | 4 | 4 | 4 | 4 | — | — | — | — |
| RE-4 (Concentration: 50 wt. %) | — | — | — | — | — | 4 | 4 | 4 | 4 |
| Mineral oil 50SUS (37.8° C.) | 21 | — | 7 | — | — | 21 | — | 7 | — |
| Isohexadecane | — | 21 | — | — | — | — | 21 | — | — |
| Sunflower oil | — | — | 7 | — | — | — | — | 7 | — |
| Caprylyl methicone (FZ-3196) | — | — | 7 | 13.5 | 21 | — | — | 7 | 13.5 |
| 2-Ethylhexyl methoxycinnamate | — | — | — | 7.5 | — | — | — | — | 7.5 |
| Sodium chloride | 0.5 | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 | 68.5 |
| 1,3-Butylene glycol | 6 | 6 | 6 | 6 | 6 | 6 | 6 | 6 | 6 |
| Homogeneity of oil phase | ○ | ○ | ○ | ○ | ○ | Separated | Separated | Separated | Separated |

TABLE 3-continued

Water-in-oil emulsion composition formulations and evaluation results
(Practical Examples 7 and 11 and Comparative Examples 12 to 15)

| Raw material name & silicone compound No. | Practical Example | | | | | Comparative Example | | | |
|---|---|---|---|---|---|---|---|---|---|
| | 7 | 8 | 9 | 10 | 11 | 12 | 13 | 14 | 15 |
| Emulsion viscosity (25° C.)[Pa · s] | 88 | 32 | 130 | 104 | 67 | — | — | — | — |
| Weight average particle size Day after preparation (μm) | 2.8 | 4.2 | 2.9 | 2.2 | 4.6 | — | — | — | — |
| Weight average particle size After one month (50° C.) (μm) | 4.7 | 4.2 | 3.0 | 2.7 | 4.9 | — | — | — | — |
| Stability of emulsified particles | ○ | ◎ | ◎ | ◎ | ◎ | X | X | X | X |
| Emulsion thickening effect | ◎ | ○ | ◎ | ◎ | ◎ | X | X | X | X |

TABLE 4

Water-in-oil emulsion composition formulations and evaluation results
(Practical Examples 7 and 12 to 15 and Comparative Examples 12, 16, and 17)

| Raw material name and silicone compound No. | Practical Example | | | | | Comparative Example | | |
|---|---|---|---|---|---|---|---|---|
| | 7 | 12 | 13 | 14 | 15 | 12 | 16 | 17 |
| No. 2 (Concentration: 50 wt. %) | 4 | 2 | 2 | 1.2 | — | — | — | — |
| No. 3 (Concentration: 100 wt. %) | — | 1 | — | 0.7 | 1 | — | — | — |
| No. 4 (Concentration: 100 wt. %) | — | — | 1 | 0.7 | 1 | — | — | — |
| RE-3 (Concentration: 100 wt. %) | — | — | — | — | — | — | 2 | — |
| RE-4 (Concentration: 50 wt. %) | — | — | — | — | — | 4 | — | 4 |
| Mineral oil 50SUS (37.8° C.) | 21 | 22 | 22 | 22.4 | 23 | 21 | 23 | — |
| Caprylyl methicone (FZ-3196) | — | — | — | — | — | — | — | 21 |
| Sodium chloride | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 |
| 1,3-Butylene glycol | 6 | 6 | 6 | 6 | 6 | 6 | 6 | 6 |
| Homogeneity of oil phase | ○ | ○ | ○ | ○ | ◎ | Separated | ◎ | Δ |
| Emulsion viscosity (25° C.)[Pa · s] | 88 | 27 | 42 | 23 | 23 | — | 12 | 60 |
| Weight average particle size Day after preparation (μm) | 2.8 | 3.3 | 3.2 | 3.1 | 3.2 | — | 5.3 | 4.3 |
| Weight average particle size After one month (50° C.) (μm) | 4.7 | 3.1 | 3.4 | 3.1 | 3.3 | — | Separated | 5.3 |
| Stability of emulsified particles | ○ | ◎ | ◎ | ◎ | ◎ | X | X | ○ |
| Emulsion thickening or viscosity adjustment | | Performed freely | | | Difficult | X | X | Possible |

It can be seen from the above results that the long-chain alkyl group-containing high-molecular-weight diglycerin derivative-modified silicones No. 1 and No. 2 of the present invention have an outstanding thickening effect and pure emulsification/dispersion performance when the oil phase is a continuous phase. In particular, it can be seen that these silicones have the excellent property that a high-viscosity emulsion can be provided by finely and stably emulsifying and dispersing an aqueous (or polyol) phase, which makes it possible to provide a highly reliable composition with excellent stability over time and with regard to heat, not only when the oil phase is a silicone oil or a mixed oil of a silicone oil and an ester oil agent, but also when the oil phase primarily consists of a non-polar organic oil such as a mineral oil or isohexadecane, with which stabilization has been difficult using conventional glycerin-modified silicones. Here, in Practical Example 8, the emulsion viscosity is a lower value (32 [Pa·s]) than in the other practical examples, but this is because the emulsified isohexadecane (light liquid isoparaff in) is non-polar and has a very low viscosity (4 [Pa·s] at 25° C.), and it can be seen that a stable high-viscosity emulsion can be formed even with such a low-viscosity non-polar oil agent. In addition, from these results, the two types of long-chain alkyl group-containing high-molecular-weight diglycerin derivative-modified silicones of the present invention, that is, No. 1 and No. 2, which have roughly same number average molecular weights but have different alkyl group contents (different ranges of compatible oil agent types), can also be used in combination for emulsification at an appropriate ratio, so this can be considered a preferable technique.

Further, it was verified that with a technique of using the silicone compound No. 3 or No. 4, which are a long-chain alkyl group-containing high-molecular-weight diglycerin derivative-modified silicon and a specific long-chain alkyl group-containing low-molecular-weight diglycerin derivative-modified silicon having a number average molecular weight of less than 20,000 of the present invention in combination at a desired ratio {that is, a technique of implementing the formulation design of a water (or polyol)-in-oil emulsion composition by combining two types of emulsifiers of different molecular weights, each having an outstanding emulsification performance alone}, the viscosity range of the emulsion can be controlled discretionarily and easily without using a separate oil thickening agent. Moreover, it is verified that a highly reliable composition in which an aqueous (or polyol) phase is finely and stably emulsified and dispersed and which has excellent stability over time and with regard to heat can be obtained, even when the oil phase primarily consists of a non-polar organic oil such as a mineral oil or isohexadecane, with which stabilization has been difficult using conventional glycerin-modified silicones. That is, with this technique, it is possible to provide a practical W/Oemulsifier (or emulsifier composition) not containing a compound having a polyoxyethylene (PEG) structure, wherein the emulsifier is capable of demonstrating not only compatibility with a wide range of oil agent types, but also a wide range of compatibility with regard to the viscosity range of the obtained emulsion.

Accordingly, in concert with the global trend of improving the structure of end consumer products such as cosmetics or external use preparations to PEG-FREE formulations on the whole using the excellent properties of the present invention, an emulsifier for a water (or polyol)-in-oil emulsion containing the long-chain alkyl group-containing high-molecular-weight diglycerin derivative-modified silicone of the present invention makes it possible to realize a water-in-oil (or polyol-in-oil) emulsion external use preparation or cosmetic composition which exhibits excellent stability, usability, and tactile sensation in spite of not containing a compound having a polyoxyethylene portion, or a highly reliable external use preparation or cosmetic composition containing the emulsion composition. An emulsifier is a material with an important position of forming the basic skeleton of an emulsion formulation, and the completion of this technology means that a PEG-FREE practical O/W emulsification system is complete.

It can be seen that the technique of Practical Example 15 {technique for designing and producing a water (or polyol)-in-oil emulsion composition, a cosmetic composition, or the like using two types of specific long-chain alkyl group-containing low-molecular-weight diglycerin derivative-modified silicones, each capable of providing a stable emulsion with outstanding emulsification performance and low viscosity when used alone, as emulsifiers} has a low degree of freedom for controlling the viscosity of an emulsion composition to a high level when used alone. However, depending on the application of the cosmetic composition or external use preparation, there are cases in which there is a demand for a stable emulsion with a low viscosity or cases in which the fine particle dispersion of a powder component into the oil phase must be performed simultaneously during the emulsification process (so-called cases in which it is desirable to make an emulsifier also function as a powder surface treatment agent or a powder dispersant). It is appropriate to use the technique of Practical Example 15 in such cases. Rather than the conventional philosophy of using an auxiliary emulsifier together with a primary emulsifier, a technique of blending two types of excellent emulsifiers into the emulsification system in combination is thought to have substantial advantages. As a result, it is possible to reduce the risk of product recalls due to stability defects in the cosmetic composition or external use preparation serving as an end product (clear abnormalities in the appearance that can be easily discerned by consumers, such as separation or aggregation). When two or more types of emulsifiers are used, it is possible to further reduce the risk of affecting the overall quality of the end product due to a given emulsifier in comparison to cases in which only one type is used. From such a perspective, the compounding ratio of the two types of long-chain alkyl group-containing diglycerin derivative-modified silicones is preferably in a range of approximately 4:6 to approximately 6:4.

Hereinafter, formulation examples of the cosmetic composition and the external use preparation of the present invention are described, but it is understood that the cosmetic composition and the external use preparation of the present invention are not limited to the types and compositions recited in these formulation examples.

The long-chain alkyl group-containing high-molecular-weight diglycerin derivative-modified silicone or the like of the present invention can be used in various external use preparations and cosmetic compositions. Specific formulation examples thereof include examples in which components corresponding to silicone compound No. 1 to No. 16 in the formulation examples of various cosmetic compositions and external use preparations disclosed in the practical examples and the like of Patent Document 8 (WO/2011/049248) are substituted with the "long-chain alkyl group-containing high-molecular-weight diglycerin derivative-modified silicone" of the present invention (for example, silicone compound No. 1 or No. 2 or a mixture comprising an appropriate ratio thereof). Further, examples in which components corresponding to silicone compound No. 1 to No. 16 in the formulation examples of various cosmetic compositions and external use preparations disclosed in the practical examples and the like of Patent Document 8 are substituted with a mixture of the "long-chain alkyl group-containing high-molecular-weight diglycerin derivative-modified silicone" and the "long-chain alkyl group-containing-molecular-weight diglycerin derivative-modified silicone" of the present invention (for example, a combination with silicone compound No. 1 or No. 2, or a combination with silicone compound No. 3 or No. 4 at an appropriate compounding ratio) are also included in the scope of the present invention as formulation examples of the cosmetic composition and external use preparation of the present invention.

Further, when a surfactant or emulsifier is also required to have the function of a powder surface treatment agent or a powder dispersant, it is preferable to use a system having a chemical structure with a relatively low molecular weight. Accordingly, it is optimal to use the "long-chain alkyl group-containing low-molecular-weight diglycerin derivative-modified silicone" of the present invention (for example, silicone compound No. 3 or No. 4, or a mixture comprising an appropriate ratio thereof) in place of the compounds of the practical examples and formulation examples containing silicone compound Nos. 9 to 12, 14, and 15 in Patent Document 8. On the other hand, with regard to the practical examples and formulation examples containing silicone compound Nos. 1 to 8, 13, and 16 in Patent Document 8, it is optimal to use the "long-chain alkyl group-containing high-molecular-weight diglycerin derivative-modified silicone" of the present invention (for example, silicone compound No. 1 or No. 2, or a mixture comprising an appropriate ratio thereof) or the "long-chain alkyl group-containing low-molecular-weight diglycerin derivative-modified silicone" of the present invention (for example, a combination with silicone compound No. 1 or No. 2, or a combination with silicone compound No. 3 or No. 4 at an appropriate compounding ratio) in place of these compounds. As a result, improvements in the effects of various cosmetic compositions or external use preparations can be anticipated, and the reliability from the perspective of the long-term storage stability also improves.

In addition, formulations in which components corresponding to silicone compound No. 1 to No. 16 in the formulation examples of various cosmetic compositions and external use preparations disclosed in the practical examples and the like of Patent Document 8 (WO/2011/049248) are substituted with the long-chain alkyl group-containing high-molecular-weight diglycerin derivative-modified silicone or the like of the present invention or, when a compound comprising a polyoxyethylene group or a polyoxyethylene portion is used in the formulation, formulations in which the components are substituted with an optional substitute material with a non-PEG structure or the long-chain alkyl group-containing high-molecular-weight diglycerin derivative-modified silicone of the present invention, are also suitably included in the scope of the present invention as formulation examples of the cosmetic composition or external use preparation of the present invention. For example, in compositions using polyether-modified silicones in these formulation examples, it is possible to design and put into practical application PEG-FREE formulations by substituting the components with the long-chain alkyl group-containing high-molecular-weight diglycerin derivative-modified silicone of the present invention or a mixture of this silicone and the long-chain alkyl group-containing low-molecular-weight diglycerin derivative-modified silicone of the present invention.

Specifically, the practical examples and the like in Patent Document 8 disclose emulsions, lip glosses, oil-based foundations, water-in-oil emulsion transparent antiperspirant compositions, and non-aqueous stick-form antiperspirant compositions as compositions which can be substituted by or added to the long-chain alkyl group-containing high-molecular-weight diglycerin derivative-modified silicone or the like of the present invention, and the following formulation examples are disclosed in paragraphs [0459] to [0501]. By using the long-chain alkyl group-containing high-molecular-weight diglycerin derivative-modified silicone or the like of the present invention, the stability over time or with respect to temperature further improves when the dosage form is a W/O emulsion. In addition, since the silicone has excellent compatibility with a wide range of organic oils in addition to silicone oils, the homogeneity or compounding stability further improves in non-aqueous formulations or formulations containing powders, and the effect and grade as a cosmetic composition are thus enhanced. In particular, for the applications and formulations disclosed in Patent Document 8, the diglycerin derivative-modified silicone of the present invention is useful in that it can be substituted or added to a wide range of compositions, even with a wide range of structures having a relatively low molecular weight or having polysiloxane chains with a low to high degree of polymerization.

[Example 1: emulsion foundation]; [Example 2: liquid foundation]; [Example 3: foundation]; [Example 4: water-in-oil cream]; [Example 5: water-in-oil emulsion composition]; [Example 6: water-in-oil emulsion lipstick (liquid)]; [Example 7: liquid lipstick]; [Example 8: lipstick]; [Example 9: sunscreen emulsion]; [Example 10: emulsion]; [Example 11: sun-blocking cream]; [Example 12: UV-blocking water-in-oil emulsion]; [Example 13: sunscreen]; [Example 14: water-in-oil emulsion sunscreen]; [Example 15: O/W cream]; [Example 16: eye shadow]; [Example 17: mascara]; [Example 18: mascara]; [Example 19: solid powder eye shadow]; [Example 20: pressed powderized cosmetic composition]; [Example 21: powder foundation]; [Example 22: pressed foundation]; [Example 23: cream]; [Example 24: foundation]; [Example 25: water-in-oil sun-blocking agent]; [Example 26: lipstick]; [Example 27: lipstick]; [Example 28: foundation]; [Example 29: antiperspirant aerosolized cosmetic]; [Example 30: non-aqueous pressure antiperspirant product]; [Example 31: aerosol antiperspirant composition]; [Example 32: antiperspirant lotion composition]; [Example 33: W/O emulsion-type skin external use preparation]; [Example 34: non-aqueous antiperspirant deodorant stick composition]; [Example 35: W/O solid antiperspirant stick composition]; [Example 36: W/O emulsion-type antiperspirant cream composition]; [Example 37: mascara]; [Example 38: aftershave cream]; [Example 39: solid foundation]; [Example 40: daytime whitening cream]; [Example 41: suntan cream]; [Example 42: polyol/O-type non-aqueous emulsion skin external use preparation]; [Example 43: polyol/O-type non-aqueous emulsion skin external use preparation]

In addition, formulations in which components corresponding to silicone compound No. 1 to No. 14 in the formulation examples of various cosmetic compositions and external use preparations disclosed in the practical examples and the like of Patent Document 9 (WO/2011/049247) are substituted with the "long-chain alkyl group-containing high-molecular-weight diglycerin derivative-modified silicone" of the present invention (for example, silicone compound No. 1 or No. 2, or a mixture comprising an appropriate ratio thereof) are also included in the scope of the present invention as formulation examples of the cosmetic composition or external use preparation of the present invention. As a result, improvements in the effects of various cosmetic compositions or external use preparations can be anticipated, and the reliability from the perspective of the long-term storage stability also improves.

In addition, formulations in which components corresponding to silicone compound No. 1 to No. 14 in the formulation examples of various cosmetic compositions and external use preparations disclosed in the practical examples and the like of Patent Document 9 (WO/2011/049247) are substituted with the "long-chain alkyl group-containing high-molecular-weight diglycerin derivative-modified silicone" of the present invention, or when a compound containing a polyoxyethylene group or a polyoxyethylene portion is used in the formulation, formulations in which the components are substituted with an optional substitute material with a non-PEG structure, are also suitably included in the scope of the present invention as formulation examples of the cosmetic composition or external use preparation of the present invention. For example, in compositions using polyether-modified silicones in these formulation examples, it is possible to design and put into practical application PEG-FREE formulations by substituting the components with the long-chain alkyl group-containing high-molecular-weight diglycerin derivative-modified silicone of the present invention or a mixture of this silicone and the long-chain alkyl group-containing low-molecular-weight diglycerin derivative-modified silicone of the present invention.

Specifically, as compositions replaceable by the long-chain alkyl group-containing high-molecular-weight diglycerin derivative-modified silicone or the like of the present invention, lipsticks, gel-like compositions, emulsified cosmetic compositions, and water-in-oil emulsion type transparent soft gel antiperspirants are disclosed in the practical examples and the like in Patent Document 9. In addition, the following formulation examples are disclosed in paragraphs [0375] to [0400]. By using the long-chain alkyl group-containing high-molecular-weight diglycerin derivative-modified silicone or the like of the present invention, the stability over time or with respect to temperature further improves when the dosage form is a W/O emulsion. In addition, since the silicone has excellent compatibility with a wide range of organic oils in addition to silicone oils, the homogeneity or compounding stability further improves in non-aqueous formulations or formulations containing powders, and the effect and grade as a cosmetic composition are thus enhanced. In particular, for the applications and formulations disclosed in Patent Document 9, the diglycerin derivative-modified silicone of the present invention is useful in that it can be suitably substituted or added to compositions, in a structure having a relatively high molecular weight or having polysiloxane chains with a high degree of polymerization.

[Example 1: lipstick]; [Example 2: lipstick]; [Example 3: lipstick]; [Example 4: lipstick]; [Example 5: oil-based solid eye shadow]; [Example 6: eye liner]; [Example 7: foundation]; [Example 8: foundation]; [Example 9: gel-like cosmetic composition]; [Example 10: cream-like emulsion cosmetic composition]; [Example 11: paste-like emulsion cosmetic composition]; [Example 12: aerosol antiperspirant composition]; [Example 13: gel-like antiperspirant stick]; [Example 14: oil-based gel cleansing agent]; [Example 15: gel-like antiperspirant stick]; [Example 16: gel-like deodorant stick]; [Example 17: gel-like cream]; [Example 18: gel-like lip cream]; [Example 19: mascara]; [Example 20: gel-like aftershave cream]; [Example 21: solid foundation]; [Example 22: gel-like daytime whitening cream]; [Example 23: polyol/O-type non-aqueous gel emulsion skin external use preparation]; [Example 24: polyol/O-type non-aqueous gel emulsion skin external use preparation]

Further, formulations in which components corresponding to silicone compound No. 1 to No. 8 in the formulation examples of various cosmetic compositions and external use preparations disclosed in the practical examples and the like of Patent Document 10 (Japanese Unexamined Patent Application Publication No. 2012-046507A) are substituted with the "long-chain alkyl group-containing high-molecular-weight diglycerin derivative-modified silicone" of the present invention (for example, silicone compound No. 1 or No. 2, or a mixture comprising an appropriate ratio thereof) are also included in the scope of the present invention as formulation examples of the hair cosmetic composition external use preparation of the present invention. As a result, improvements in the effects of various hair cosmetic compositions or external use preparations can be anticipated, and the reliability from the perspective of the long-term storage stability also improves.

Specifically, as compositions replaceable by the long-chain alkyl group-containing high-molecular-weight diglycerin derivative-modified silicone or the like of the present invention, hair conditioners, shampoos, and hair creams (set type) are disclosed in the practical examples and the like in Patent Document 10. In addition, the following formulation examples are disclosed in paragraphs [0275] to [0307]. By using the long-chain alkyl group-containing high-molecular-weight diglycerin derivative-modified silicone or the like of the present invention, improvements in the effects of various hair cosmetic compositions or external use preparations can be anticipated, and the reliability from the perspective of the long-term storage stability also improves.

[Example 1: shampoo]; [Example 2: conditioner]; [Example 3: hair treatment (rinse type)]; [Example 4: hair treatment (leave-on type)]; [Example 5: hair mist]; [Example 6: hair foam]; [Example 7: hair spray]; [Example 8: hair wax]; [Example 9: hair cream]; [Example 10: hair lotion]; [Example 11: hair oil]; [Example 12: hair color (oxidation type)]; [Example 13: hair manicure]; [Example 14: perm]

The invention claimed is:

1. A composition containing (A) a diglycerin derivative-modified silicone, wherein the diglycerin derivative-modified silicone (A) is a mixture of the following:
   (A1) a high-molecular-weight diglycerin derivative-modified silicone with a number average molecular weight of at least 20,000 having a halogen atom-substituted or unsubstituted monovalent hydrocarbon group having from 9 to 30 carbon atoms in a molecule and having as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %; and
   (A2) a low-molecular-weight diglycerin derivative-modified silicone with a number average molecular weight of less than 20,000 having a halogen atom-substituted or unsubstituted monovalent hydrocarbon group having from 9 to 30 carbon atoms in a molecule and having as a hydrophilic group only a glycerin derivative group not having an oxyalkylene structure with an average value of a number of repetitions of oxyalkylene units of two or more, an average value of a number of repetitions of glycerin units being in a range of 1.5 to 2.4, the diglycerin derivative-modified silicone not having other hydrophilic groups in the molecule, and a ratio occupied by the monovalent hydrocarbon group in the molecule being at least 0.5 mass %.

2. The composition according to claim 1, wherein at least one of the diglycerin derivative-modified silicones (A1) and (A2) is represented by the following general formula (1):

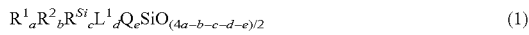

wherein
- $R^1$ is a halogen atom-substituted or unsubstituted monovalent hydrocarbon group having from 1 to 8 carbon atoms, an alkoxy group, a hydrogen atom, or a hydroxyl group;
- $R^2$ is a halogen atom-substituted or unsubstituted monovalent hydrocarbon group having from 9 to 30 carbon atoms;
- $R^{Si}$ is a chain organosiloxane group represented by the following general formula (2-1):

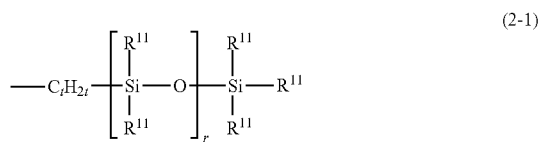

wherein $R^{11}$ is a halogen atom-substituted or unsubstituted monovalent hydrocarbon group having from 1 to 30 carbon atoms, a hydroxyl group, or a hydrogen atom, and at least one of the $R^{11}$ moieties is the monovalent hydrocarbon group; t is a number in a range of 2 to 10; and r is a number in a range of 1 to 500; or the following general formula (2-2):

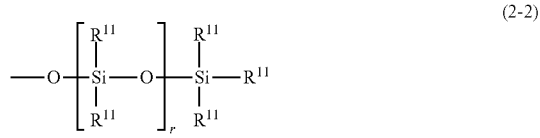

wherein $R^{11}$ and r are synonymous with those described above;

$L^1$ represents a silylalkyl group having the siloxane dendron structure represented by the following general formula (3) when i=1;

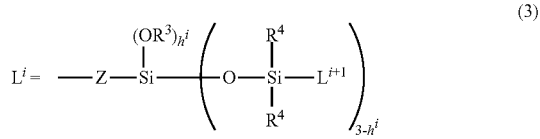

wherein $R^3$ is a halogen atom-substituted or unsubstituted, straight-chain or branched monovalent hydrocarbon group having from 1 to 30 carbon atoms; $R^4$ is each independently an alkyl group or phenyl group having from 1 to 6 carbon atoms; Z is a divalent organic group; i is a generation of the silylalkyl group represented by $L^i$ and is an integer of 1 to k when k is a number of generations serving as a number of repetitions of the silylalkyl group; the number of generations k is an integer from 1 to 10; $L^{i+1}$ is the silylalkyl group when i is less than k, and $R^4$ when i=k; and $h^i$ is a number in a range of 0 to 3;

Q is a glycerin derivative group having an average value of the number of repetitions of glycerin units in a range of 1.5 to 2.4; and a, b, c, d, and e are numbers in ranges so that $0 \leq a \leq 2.5$, $0 < b \leq 1.5$, $0 \leq c + d \leq 1.5$, and $0.001 \leq e \leq 1.5$.

3. The composition according to claim 1, wherein at least one of the diglycerin derivative-modified silicones (A1) and (A2) has the following provisions: wherein the glycerin derivative group is a diglycerin derivative group-containing organic group bonded to a silicon atom via a divalent linking group and comprising at least one type of glycerin unit selected from hydrophilic units represented by the following structural formulae (4-1) to (4-3), wherein a number of repetitions thereof is in a range of 1.5 to 2.4 on average, the substance not having an oxyalkylene structure having an average value of the number of repetitions of oxyalkylene units of two or more in the same group:

wherein W is a hydrogen atom or an alkyl group having from 1 to 20 carbon atoms;

wherein W is synonymous with the group described above;

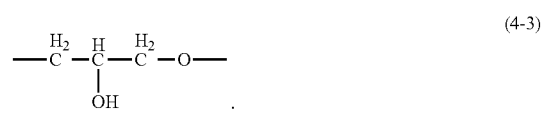

4. The composition according to claim 1, wherein at least one of the diglycerin derivative-modified silicones (A1) and (A2) has the following provisions: wherein the glycerin derivative group is a diglycerin derivative group-containing organic group represented by the following general formula (5-1):

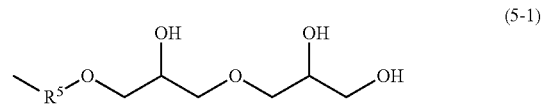

wherein $R^5$ is a divalent organic group that does not have an oxyalkylene structure with an average value of the number of repetitions of oxyalkylene units of two or more; or the following general formula (5-2):

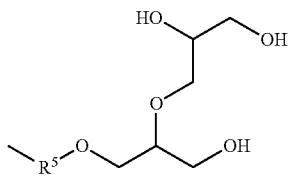

(5-2)

wherein $R^5$ is synonymous with those described above.

5. The composition according to claim 1, wherein at least one of the diglycerin derivative-modified silicones (A1) and (A2) is represented by the following structural formula (1-1):

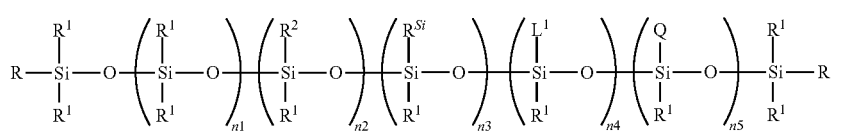

(1-1)

wherein $R^1$ is a halogen atom-substituted or unsubstituted monovalent hydrocarbon group having from 1 to 8 carbon atoms, an alkoxy group, a hydrogen atom, or a hydroxyl group;

$R^2$ is a halogen atom-substituted or unsubstituted monovalent hydrocarbon group having from 9 to 30 carbon atoms;

$R^{Si}$ is a chain organosiloxane group represented by the following general formula (2-1):

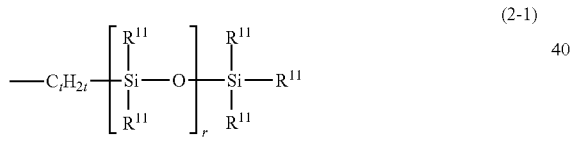

(2-1)

wherein $R^{11}$ is a halogen atom-substituted or unsubstituted monovalent hydrocarbon group having from 1 to 30 carbon atoms, a hydroxyl group, or a hydrogen atom, and at least one of the $R^{11}$ moieties is the monovalent hydrocarbon group; t is a number in a range of 2 to 10; and r is a number in a range of 1 to 500; or the following general formula (2-2):

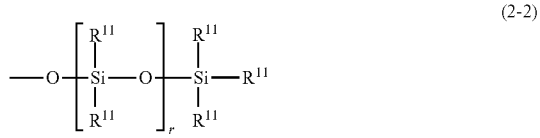

(2-2)

wherein $R^{11}$ and r are synonymous with those described above;

$L^1$ represents a silylalkyl group having the siloxane dendron structure represented by the following general formula (3) when i=1;

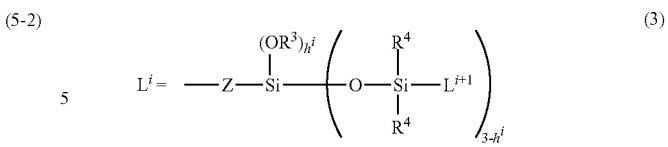

(3)

wherein $R^3$ is a halogen atom-substituted or unsubstituted, straight-chain or branched monovalent hydrocarbon group having from 1 to 30 carbon atoms; $R^4$ is each independently an alkyl group or phenyl group having from 1 to 6 carbon atoms; Z is a divalent organic group; i is a generation of the silylalkyl group represented by $L^i$ and is an integer of 1 to k when k is a number of generations serving as a number of repetitions of the silylalkyl group; the number of generations k is an integer from 1 to 10; $L^{i+1}$ is the silylalkyl group when i is less than k, and $R^4$ when i=k; and $h^i$ is a number in a range of 0 to 3;

Q is a glycerin derivative group having an average value of the number of repetitions of glycerin units in a range of 1.5 to 2.4; and R is a group selected from $R^1$, $R^2$, $R^{Si}$, $L^1$, and Q;

(n1+n2+n3+n4+n5) is a number in a range of 201 to 1200; n1 is a number in a range of 100 to 1000; n2 is a number in a range of 0 to 500; n3 is a number in a range of 0 to 100; n4 is a number in a range of 0 to 100; and n5 is a number in a range of 0 to 100; provided when n2=0, at least one R moiety is $R^2$, and when n5=0, at least one R moiety is Q.

6. The composition according to claim 1, wherein at least one of the diglycerin derivative-modified silicones (A1) and (A2) has the following provision: wherein a ratio occupied by the monovalent hydrocarbon group in the molecule is at most 50 mass %.

7. The composition according to claim 1, wherein at least one of the diglycerin derivative-modified silicones (A1) and (A2) has the following provision: wherein a ratio occupied by the monovalent hydrocarbon group in the molecule is at least 15 mass % and at most 40 mass %.

8. The composition according to claim 1, wherein the composition is at least one functional material selected from the group consisting of surfactants, dispersants, and thickening agents.

9. The composition according to claim 1, wherein the composition is a thickening emulsifier for a water-in-oil emulsion or a polyol-in-oil emulsion.

10. The composition according to claim 1, wherein the composition does not contain a compound having an oxyalkylene structure having an average value of the number of repetitions of oxyalkylene units of two or more.

11. An external use preparation containing the composition according to claim 1.

12. A cosmetic composition containing the composition according to claim 1.

13. The composition according to claim 1, further defined as a water-in-oil emulsion.

14. The composition according to claim 1, further defined as a polyol-in-oil emulsion.

15. The composition according to claim 1, further containing (B) water and/or (C) an oil agent.

16. The composition according to claim 1, further containing (D) a film-forming agent.

17. The composition according to claim 1, further containing one or more components selected from the group consisting of (E) a powder or coloring agent, (K) an ultraviolet light blocking component, and (N) a bioactive component.

18. The composition according to claim 1, further containing (G) a polyol.

* * * * *